(12) United States Patent
Tobler et al.

(10) Patent No.: US 7,994,341 B2
(45) Date of Patent: Aug. 9, 2011

(54) PROCESS FOR THE PRODUCTION OF AMIDES

(75) Inventors: Hans Tobler, Basel (CH); Harald Walter, Basel (CH); Josef Ehrenfreund, Basel (CH); Camilla Corsi, Basel (CH); Fanny Giordano, Muenchwilen (CH); Martin Zeller, Muenchwilen (CH); Gottfried Seifert, Muenchwilen (CH); Shailesh Shah, Muenchwilen (CH); Neil George, Huddersfield (GB); Ian Kevin Jones, Huddersfield (GB); Paul Edward Bonnett, Greensboro, NC (US)

(73) Assignee: Syngenta Limited, Guildford, Surrey (GB)

( * ) Notice: Subject to any disclaimer, the term of this patent is extended or adjusted under 35 U.S.C. 154(b) by 538 days.

(21) Appl. No.: 12/066,683

(22) PCT Filed: Sep. 14, 2006

(86) PCT No.: PCT/EP2006/008982
§ 371 (c)(1),
(2), (4) Date: Jul. 16, 2008

(87) PCT Pub. No.: WO2007/031323
PCT Pub. Date: Mar. 22, 2007

(65) Prior Publication Data
US 2009/0163569 A1 Jun. 25, 2009

(30) Foreign Application Priority Data

Sep. 16, 2005 (CH) ........................... 1520/05
Feb. 24, 2006 (CH) ........................... 0296/06

(51) Int. Cl.
*C07D 231/14* (2006.01)
(52) U.S. Cl. .................. 548/365.1; 548/374.1
(58) Field of Classification Search .................. None
See application file for complete search history.

(56) References Cited

U.S. PATENT DOCUMENTS
7,732,469 B2 * 6/2010 Tobler et al. .................. 514/365

FOREIGN PATENT DOCUMENTS
WO 2004018438 3/2004
WO 2004035589 4/2004
* cited by examiner

*Primary Examiner* — Kamal Saeed
(74) *Attorney, Agent, or Firm* — Rebecca Howard

(57) ABSTRACT

The present invention relates to a process for the preparation of compounds of formula (I) wherein $R_1$ and $R_2$ are each independently of the other hydrogen or $C_1$-$C_5$alkyl and $R_3$ is $CF_3$ or $CF_2H$, by a) reaction of a compound of formula (II) wherein $R_1$ and $R_2$ are as defined for formula (I), with at least one reducing agent to form a compound of formula (III) wherein $R_1$ and $R_2$ are as defined for formula (I), and b) reaction of that compound with at least one reducing agent to form a compound of formula (IV) wherein $R_1$ and $R_2$ are as defined for formula (I), and (c) reaction of that compound with a compound of formula (V) wherein Q is chlorine, fluorine, bromine, iodine, hydroxy or $C_1$-$C_6$alkoxy and $R_3$ is as defined for formula (I), to form the compound of formula (I); and to novel intermediates for use in that process.

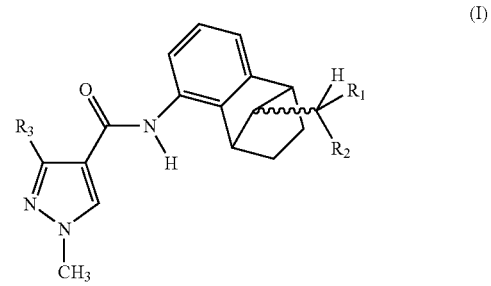

(I)

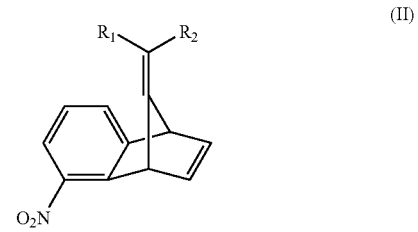

(II)

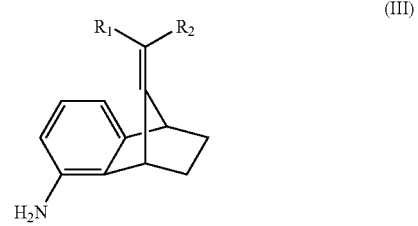

(III)

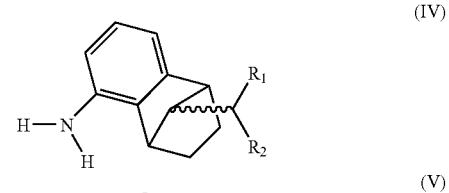

(IV)

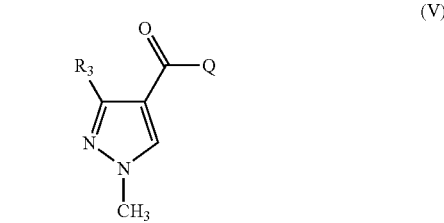

(V)

15 Claims, 4 Drawing Sheets

Figure 1: X-ray powder diffraction pattern of crystal modification B
Figure 2: X-ray powder diffraction pattern of crystal modification A
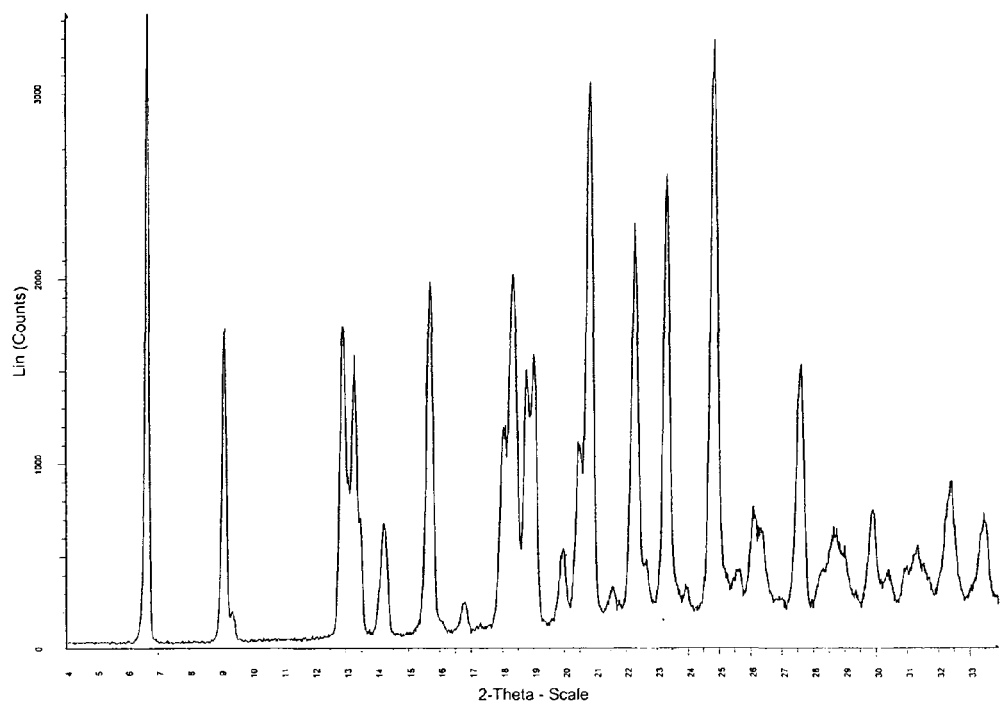

Figure 3: Raman Spectrum of crystal modification B
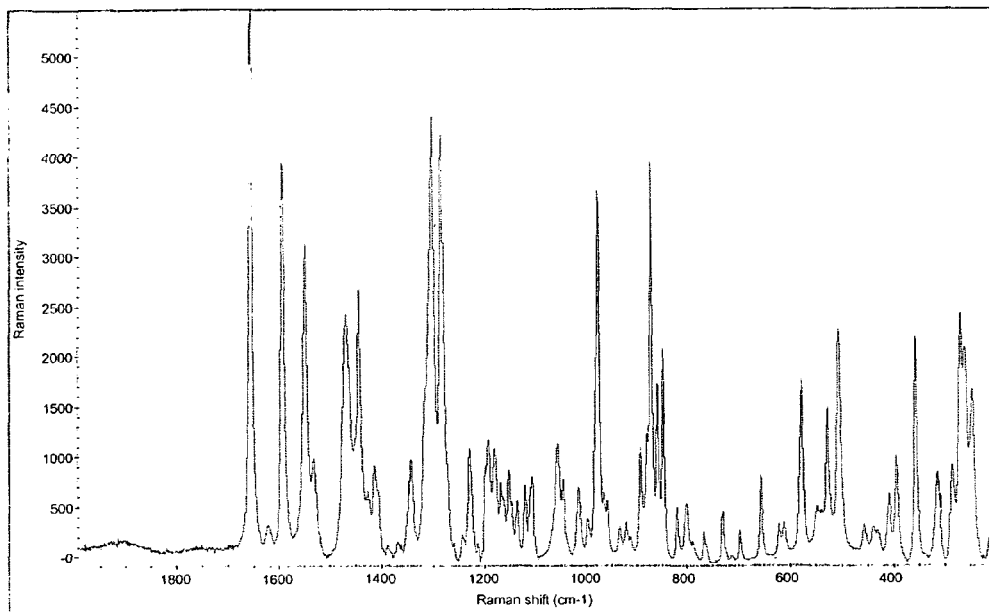
Figure 4: Raman Spectrum of crystal modification A
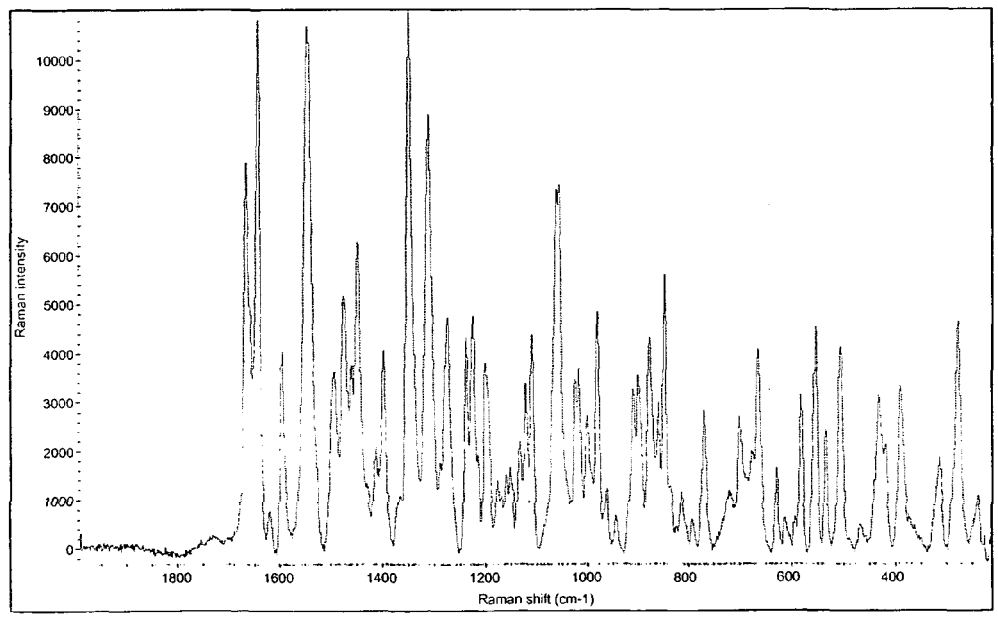

Figure 5: Thermogram in differential scanning calorimetry of crystal modification B
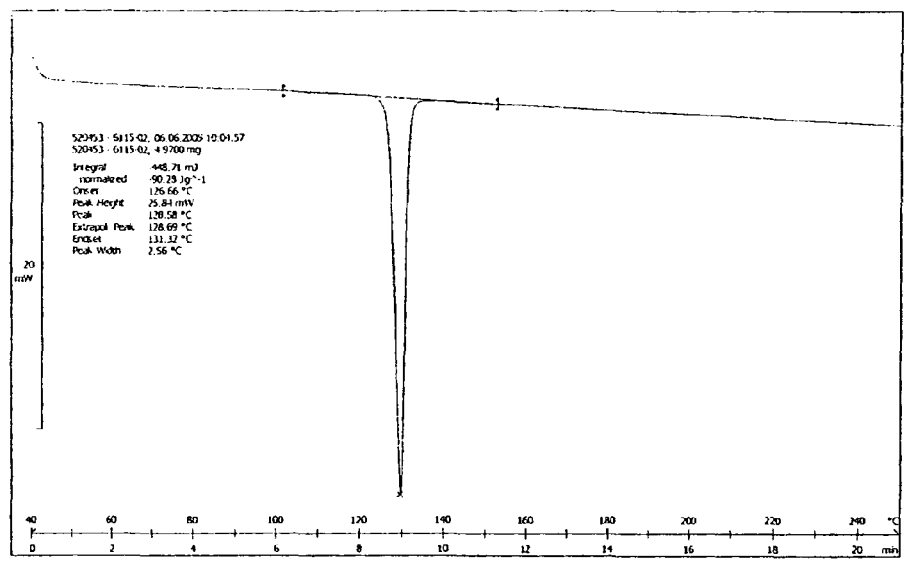
Figure 6: Thermogram in differential scanning calorimetry of crystal modification B
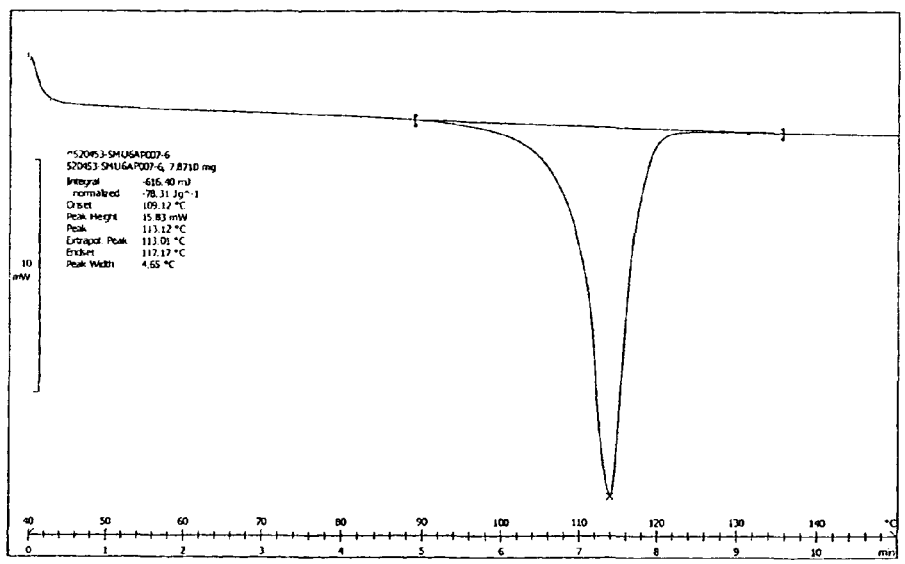

Figure 7: X-ray powder diffraction pattern of crystal modification B (syn/anti: 92:8)
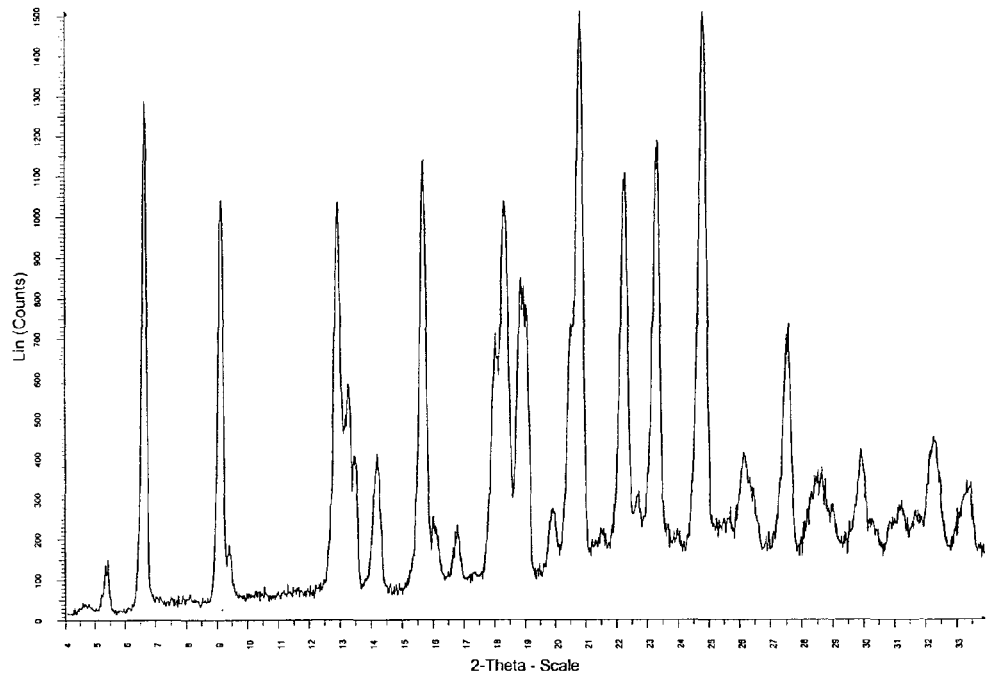
Figure 8: X-ray powder diffraction pattern of crystal modification B (syn/anti: 95:5)
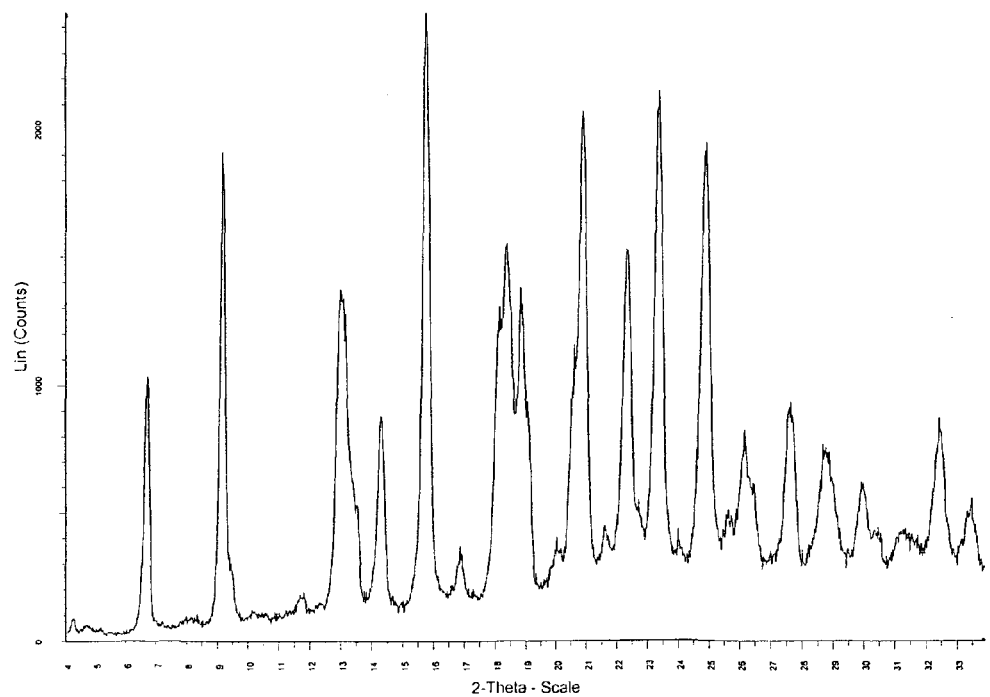

PROCESS FOR THE PRODUCTION OF AMIDES

This application is a 371 of International Application No. PCT/EP2006/008982 filed Sep. 14, 2006, which claims priority to CH 01520/05 filed Sep. 16, 2005, and CH 0296/06 filed Feb. 24, 2006, the contents of which are incorporated herein by reference.

The present invention relates to a process for the preparation of pyrazolyl-4-carboxylic acid benzonorbornen-5-yl-amides and also to novel intermediates for use in such a process. The present invention further relates to a novel crystal modification of syn-3-difluoromethyl-1-methyl-1H-pyrazole-4-carboxylic acid (9-isopropyl-1,2,3,4-tetrahydro-1,4-methano-naphthalen-5-yl)-amide, compositions comprising it and to the use thereof in the control of fungus infestation in cultivated plants.

Pyrazolyl-4-carboxylic acid benzonorbornen-5-yl-amides, for example 3-difluoromethyl-1-methyl-1H-pyrazole-4-carboxylic acid (9-isopropyl-1,2,3,4-tetrahydro-1,4-methano-naphthalen-5-yl)-amide, are valuable fungicides, such as are described, for example, in WO 04/035589.

WO 04/035589 describes a process for the preparation of pyrazolyl-4-carboxylic acid benzonorbornen-5-yl-amides (see Scheme 1):

Scheme 1:

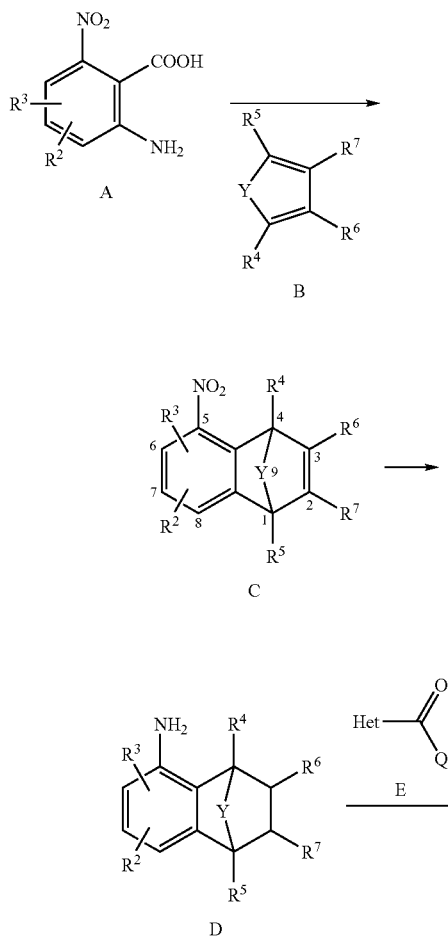

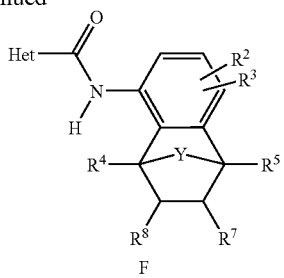

According to WO 04/035589, a 3-nitro-dehydrobenzene generated, for example, from 6-nitro-anthralinic acids of formula (A) wherein $R^2$ and $R^3$ may be, inter alia, hydrogen, is first reacted in a Diels-Alder reaction with a cyclic 1,4-diene of formula (B) wherein $R^4$, $R^5$, $R^6$ and $R^7$ may be, inter alia, hydrogen and Y may be, inter alia, —CH((i)—C$_3$H$_7$)—, to form a 5-nitro-benzonorbornadiene compound of formula (C). Subsequent catalytic reduction under standard conditions (for example, Ra/Ni or Pd/C) in a solvent (for example, methanol) reduces both the nitro group and the endocyclic double bond in the 2,3-position and yields a 5-amino-benzonorbornene of formula (D). The 5-amino-benzonorbornene of formula (D) can then be reacted with an acid derivative of formula (E), wherein Het may be, inter alia, a substituted pyrazole ring and Q is chlorine, fluorine, bromine or hydroxy, in a solvent (for example, dichloromethane), to form a pyrazolyl-4-carboxylic acid benzonorbornen-5-yl-amide of formula (F).

The reaction with compounds of formula (E) wherein Q is chlorine, fluorine or bromine takes place, for example, in the presence of a base (for example, triethylamine).

Compounds of formula (F) can also be obtained by reacting the 5-amino-benzonorbornene of formula (D) with an acid derivative of formula (E) wherein Het is as defined above and Q is hydroxy in the presence of an acid-activating agent (for example, bis(2-oxo-3-oxazolidinyl)-phosphinic acid chloride) in the presence of 2 equivalents of base.

In such a synthesis procedure, in the preparation of 9-monosubstituted pyrazolyl-4-carboxylic acid benzonorbornen-5-yl-amides a plurality of regioisomers are formed. In the preparation, for example, of the pyrazolyl-4-carboxylic acid benzonorbornen-5-yl-amide of formula (F) wherein $R^4$, $R^5$, $R^6$ and $R^7$ are hydrogen and Y is —CH((i)—C$_3$H$_7$)—, the following five regioisomers are formed at the stage of the Diels-Alder reaction to form the 5-nitro-benzonorbornadiene compound of formula (C):

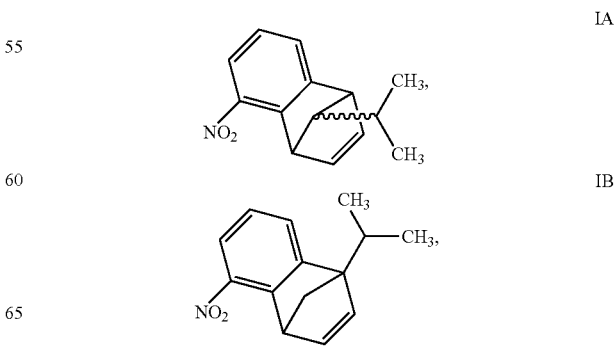

IC

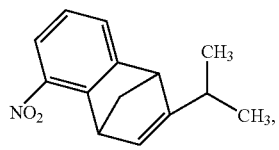

ID

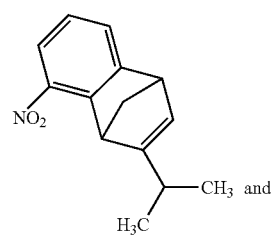

IE

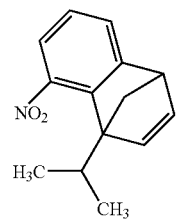

In the described preparation process, the 9-monosubstituted regioisomer (IA) is obtained only in a low yield.

The separation of the regioisomers and/or the separation of stereoisomeric forms may be carried out at the stage of the nitro-benzonorbornadiene compounds of formula (C), of the 5-amino-benzonorbornenes of formula (D) or of the pyrazolyl-4-carboxylic acid benzo-norbornen-5-yl-amides of formula (F) and is generally effected using customary methods, such as, for example, fractional crystallisation, fractional distillation or using chromatographic methods.

In view of the low yield of the 9-substituted regioisomer, such a reaction procedure is not suitable for the preparation, especially on a large scale, of 9-substituted pyrazolyl-4-carboxylic acid benzonorbornen-5-yl-amides of formula (F).

The aim of the present invention is therefore to provide a process for the preparation of 9-monosubstituted pyrazolyl-4-carboxylic acid benzonorbornen-5-yl-amides that makes it possible for those compounds to be prepared in an economically advantageous manner in high yields and in good quality.

The present invention accordingly relates to a process for the preparation of compounds of formula I

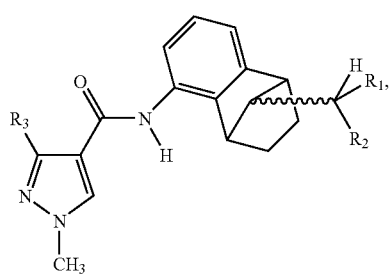

(I)

wherein $R_1$ and $R_2$ are each independently of the other hydrogen or $C_1$-$C_5$alkyl and $R_3$ is $CF_3$ or $CF_2H$, which comprises a) reacting a compound of formula II

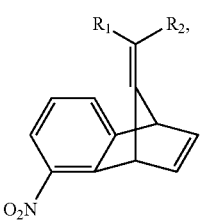

(II)

wherein $R_1$ and $R_2$ are as defined for formula I, with at least one reducing agent to form a compound of formula III

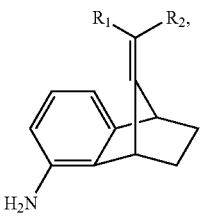

(III)

wherein $R_1$ and $R_2$ are as defined for formula I; and
(b) reacting that compound with at least one reducing agent to form a compound of formula IV

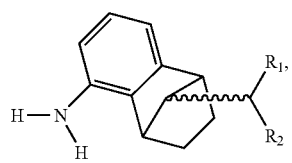

(IV)

wherein $R_1$ and $R_2$ are as defined for formula I; and
(c) converting that compound into the compound of formula I by reaction with a compound of formula V

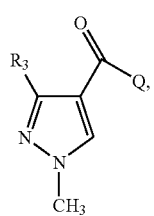

(V)

wherein Q is chlorine, fluorine, bromine, iodine, hydroxy or $C_1$-$C_6$alkoxy and $R_3$ is as defined for formula I.

The alkyl groups in the definitions of the substituents may be straight-chain or branched and are, for example, methyl ($CH_3$), ethyl ($C_2H_5$), n-propyl (n-$C_3H_7$), isopropyl (i-$C_3H_7$), n-butyl (n-$C_4H_9$), sec-butyl (sec-$C_4H_9$), isobutyl (i-$C_4H_9$), tert-butyl (tert-$C_4H_9$) and pentyl as well as the branched isomers thereof.

The alkoxy groups in the definitions of the substituents may be straight-chain or branched and are, for example, methoxy, ethoxy, n-propoxy, isopropoxy, n-butoxy, sec-butoxy, isobutoxy, tert-butoxy, pentyloxy and hexyloxy and also the branched isomers of pentyloxy and hexyloxy.

9-Monosubstituted pyrazolyl-4-carboxylic acid benzonorbornenes of formula I are chiral molecules and can occur in various stereoisomeric forms. They are shown as enantiomers of formulae $I_I$, $I_{II}$, $I_{III}$, and $I_{IV}$:

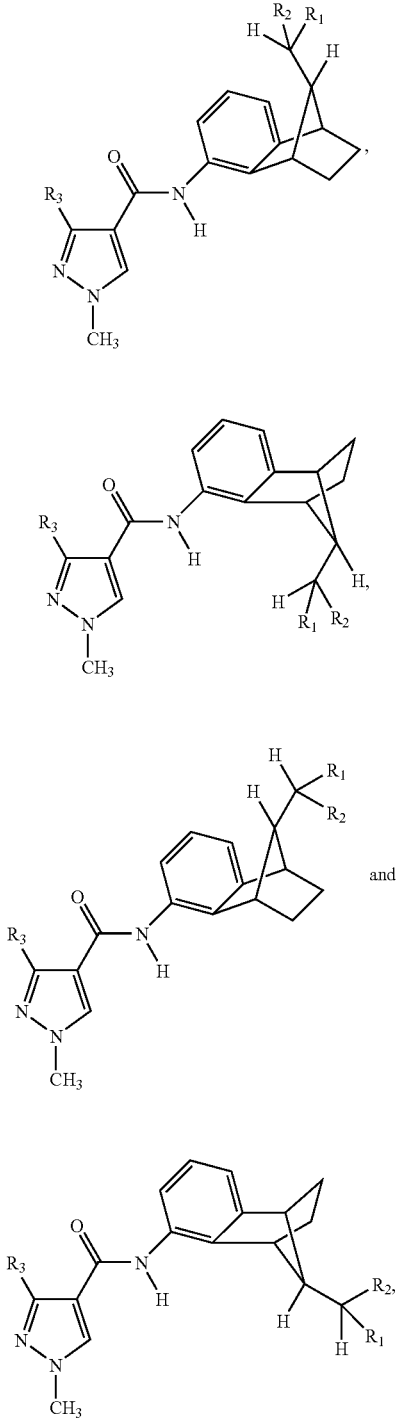

wherein $R_1$, $R_2$ and $R_3$ are as defined for formula I. The process according to the invention includes the preparation of those stereoisomeric forms of formulae $I_I$, $I_{II}$, $I_{III}$ and $I_{IV}$ and the preparation of mixtures of those stereoisomeric forms in any ratio.

In the context of the present invention, compounds of formula Ia (syn)

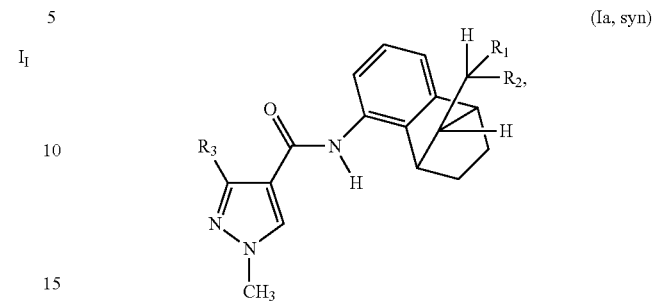

wherein $R_1$, $R_2$ and $R_3$ are as defined for formula I, are understood to be compounds of formula $I_I$; compounds of formula $I_{II}$; or a mixture, in any ratio, of compounds of formula $I_I$ and compounds of formula $I_{II}$.

In the context of the present invention, compounds of formula Ia (syn) are understood to be, preferably, a racemic mixture of compounds of formula $I_I$ and compounds of formula $I_{II}$.

In the context of the present invention, compounds of formula Ib (anti)

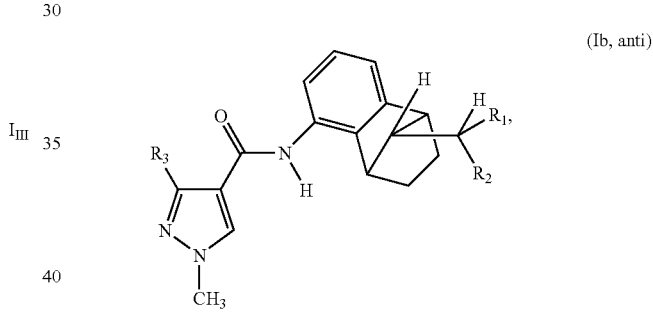

wherein $R_1$, $R_2$ and $R_3$ are as defined for formula I, are understood to be compounds of formula $I_{III}$; compounds of formula $I_{IV}$; or a mixture, in any ratio, of compounds of formula $I_{III}$, and compounds of formula $I_{IV}$.

In the context of the present invention, compounds of formula Ib (anti) are understood to be, preferably, a racemic mixture of compounds of formula $I_{III}$, and compounds of formula $I_{IV}$.

Compounds of formula IV can occur in various stereoisomeric forms, which are represented by formulae $IV_I$, $IV_{II}$, $IV_{III}$, and $IV_{IV}$:

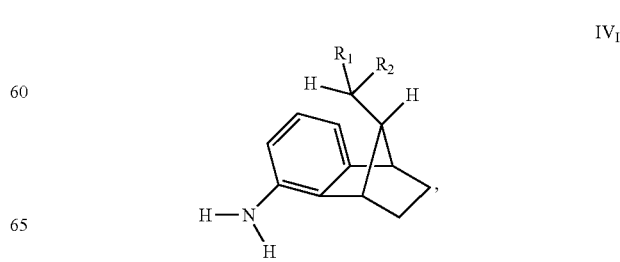

-continued

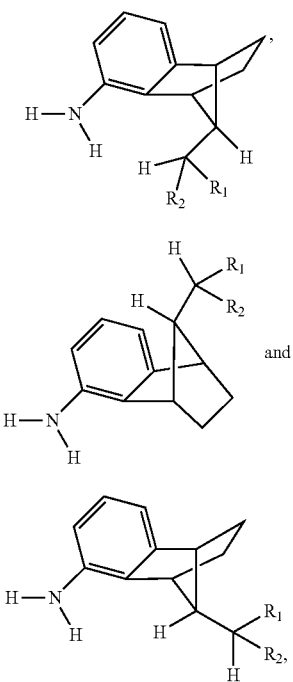

IV$_{II}$

IV$_{III}$

IV$_{IV}$ wherein $R_1$ and $R_2$ are as defined for formula I. The process according to the invention includes the preparation of those stereoisomeric forms of formulae IV$_I$, IV$_{II}$, IV$_{III}$ and IV$_{IV}$ and the preparation of mixtures of those stereoisomeric forms in any ratio.

In the context of the present invention, compounds of formula IVa (syn)

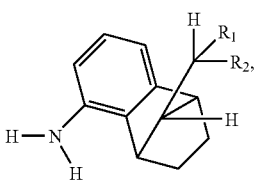

(IVa, syn)

wherein $R_1$ and $R_2$ are as defined for formula I, are understood to be compounds of formula IV$_I$; compounds of formula IV$_{II}$; or a mixture, in any ratio, of compounds of formula IV$_I$, and compounds of formula IV$_{II}$.

In the context of the present invention, compounds of formula IVa (syn) are understood to be, preferably, a racemic mixture of compounds of formula IV, and compounds of formula IV$_{II}$.

In the context of the present invention, compounds of formula IVb (anti)

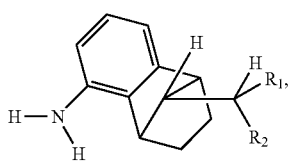

(IVb, anti)

wherein $R_1$ and $R_2$ are as defined for formula I, are understood to be compounds of formula IV$_{III}$; compounds of formula IV$_{IV}$; or a mixture, in any ratio, of compounds of formula IV$_{III}$, and compounds of formula IV$_{IV}$.

In the context of the present invention, compounds of formula IVb (anti) are understood to be, preferably, a racemic mixture of compounds of formula IV$_{III}$, and compounds of formula IV$_{IV}$.

In the context of the present invention, a "racemic mixture" of two enantiomers is understood to be a mixture of the two enantiomers in a ratio substantially equal to 1:1.

The process according to the invention is suitable especially for the preparation of compounds of formula I wherein $R_1$ and $R_2$ are methyl.

The process according to the invention is suitable very especially for the preparation of compounds of formula I wherein $R_1$ and $R_2$ are methyl and $R_3$ is $CF_2H$.

In the process according to the invention, preference is given to the use of compounds of formula II wherein $R_1$ and $R_2$ are methyl.

In the process according to the invention, preference is given to the use of compounds of formula III wherein $R_1$ and $R_2$ are methyl.

In the process according to the invention, preference is given to the use of compounds of formula IV wherein $R_1$ and $R_2$ are methyl.

Process Step a):

In one embodiment of the present invention, a single reducing agent is used in Process Step a).

A suitable reducing agent for Process Step a) is, for example, hydrogen in the presence of a metal catalyst.

Suitable amounts of reducing agent for use in Process Step a) in that embodiment of the invention are, for example, up to 4 equivalents, with preference being given to 4 equivalents for that reaction.

Process Step a) is preferably carried out in a closed vessel.

In an embodiment of the process according to the invention in which Process Step a) is carried out in a closed vessel, an excess of hydrogen is, for example, introduced into the reaction mixture in which the metal catalyst is already present. The consumption of hydrogen is then monitored over the course of the reaction time. In that embodiment of the process according to the invention, the reaction is preferably stopped when the desired amount of hydrogen has been consumed.

Suitable metal catalysts are, for example, platinum catalysts, such as, for example, platinum/carbon catalysts or $PtO_2$; palladium catalysts, such as, for example, Pd/C; rhodium catalysts, such as, for example, Rh/C, Rh/Al$_2$O$_3$ or Rh$_2$O$_3$; nickel catalysts, such as, for example, Raney nickel; or iridium catalysts, such as, for example, Ir(COD)Py(Pcy); and mixtures thereof. Preference is given to platinum catalysts, palladium catalysts, rhodium catalysts or nickel catalysts; special preference is given to palladium catalysts, rhodium catalysts or nickel catalysts; and very special preference is given to Pd/C, Rh/C or Raney nickel.

Suitable amounts of metal catalyst for that reaction are, for example, from 0.001 up to 0.5 equivalent, especially from 0.01 up to 0.1 equivalent.

That reaction is preferably carried out in the presence of an inert solvent. Suitable solvents are, for example, alcohols, such as methanol, ethanol, propanol or isopropanol, or aprotic solvents, such as tetrahydrofuran, tert-butyl methyl ether, dioxane, toluene or ethyl acetate, and mixtures thereof. Special preference is given to tetrahydrofuran or methanol.

Temperatures are generally from −40° C. to 80° C., with preference being given to a range from −20° C. to 50° C. and special preference to a range from 0° C. to 30° C. In one embodiment, the temperatures are in a range from 20 to 30° C.

The reaction may be carried out at atmospheric pressure or at elevated pressure, with preference being given to atmospheric pressure or an elevated pressure of up to 6 bar and special preference being given to atmospheric pressure.

The reaction time for that reaction is generally from 1 to 60 hours, preferably from 1 to 6 hours.

In a further embodiment of the present invention (Process Variant a2), more than one reducing agent is used in Process Step a). Preference is given to the use of two different reducing agents in successive sub-steps of the overall reduction process. The intermediates obtained in the first sub-step can be isolated by selecting suitable reaction conditions and may then be used in the second sub-step in order to form compounds of formula III.

Process Variant (a2), First Sub-step:

A suitable reducing agent for Process Variant (a2), first sub-step, is, for example, elemental iron, tin or zinc in the presence of an acid. A reducing agent to which special preference is given is elemental iron in the presence of an acid.

In one embodiment of Process Variant (a2), first sub-step, a compound of formula II

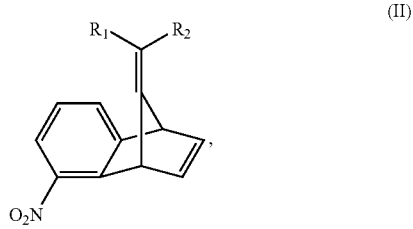

wherein $R_1$ and $R_2$ are as defined for formula I, is reacted with elemental iron in the presence of an acid to form a compound of formula IIA

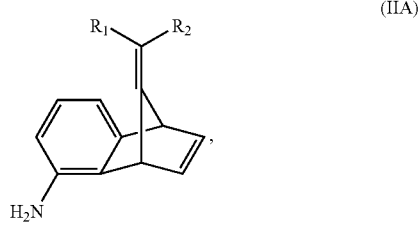

wherein $R_1$ and $R_2$ are as defined for formula I. The compounds of formula IIA can be isolated by selecting suitable reaction conditions and are then used in the second sub-step of Process Variant (a2).

The compounds of formula IIA may also be used in the second sub-step of Process Variant (a2) directly, without being isolated.

Suitable amounts of iron for the first sub-step of Process Variant (a2) are, for example, at least 5 equivalents; preferably, from 5 to 10 equivalents are used for that reaction.

Suitable acids are, for example, organic acids, such as, for example, formic acid, acetic acid or propionic acid; or inorganic acids, such as, for example, hydrochloric acid or sulfuric acid. Preference is given to organic acids and special preference is given to acetic acid.

The reaction is preferably carried out in the presence of an inert solvent. Suitable solvents are, for example, water; alcohols, such as methanol, ethanol, propanol or isopropanol; or aprotic solvents, such as tetrahydrofuran, tert-butyl methyl ether, dioxane, toluene or ethyl acetate; and mixtures thereof; alcohols are especially preferred.

Temperatures are generally from 0° C. to 120° C., with preference being given to a range from 0° C. to 100° C. and special preference to a range from 20° C. to 60° C. In one embodiment, the temperatures are in a range from 20 to 30° C.

The reaction may be carried out at atmospheric pressure or at elevated pressure.

The reaction time for that reaction is generally from 1 to 60 hours, preferably from 1 to 6 hours.

Process Variant (a2), Second Sub-step:

In the second sub-step of Process Variant (a2), the compounds formed in the first sub-step are reacted with a further reducing agent, which is different from the reducing agent in the first sub-step, to form compounds of formula III.

Suitable reducing agents for the second sub-step of Process Variant (a2) are the reducing agents mentioned for Process Step a).

Suitable amounts of reducing agent for the second sub-step of Process Variant (a2) are, for example, up to 2 equivalents; preferably, 2 equivalents are used for that reaction.

The second sub-step of Process Variant (a2) is preferably carried out in a closed vessel.

In one embodiment of the process according to the invention, in which the second sub-step of Process Variant (a2) is carried out in a closed vessel, an excess of hydrogen is, for example, introduced into the reaction mixture in which the metal catalyst is already present. The consumption of hydrogen is then monitored over the course of the reaction time. In that embodiment of the process according to the invention, the reaction is preferably stopped when the desired amount of hydrogen has been consumed.

Suitable metal catalysts are, for example, platinum catalysts, such as, for example, platinum/carbon catalysts or $PtO_2$; palladium catalysts, such as, for example, Pd/C; rhodium catalysts, such as, for example, Rh/C, Rh/$Al_2O_3$ or $Rh_2O_3$; nickel catalysts, such as, for example, Raney nickel; or iridium catalysts, such as, for example, Ir(COD)Py(Pcy); and mixtures thereof. Preference is given to platinum catalysts, palladium catalysts, rhodium catalysts or nickel catalysts; special preference is given to palladium catalysts, rhodium catalysts or nickel catalysts; and very special preference is given to Pd/C, Rh/C or Raney nickel.

Suitable amounts of metal catalyst for that reaction are, for example, from 0.001 up to 0.5 equivalent, especially from 0.01 up to 0.1 equivalent.

The reaction is preferably carried out in the presence of an inert solvent. Suitable solvents are, for example, alcohols, such as methanol, ethanol, propanol or isopropanol, or aprotic solvents, such as tetrahydrofuran, tertbutyl methyl ether, dioxane, toluene or ethyl acetate, and mixtures thereof. Special preference is given to tetrahydrofuran or methanol.

Temperatures are generally from −40° C. to 80° C., with preference being given to a range from −20° C. to 50° C. and special preference to a range from 0° C. to 30° C. In one embodiment, the temperatures are in a range from 20° C. to 30° C.

The reaction may be carried out at atmospheric pressure or at elevated pressure, with preference being given to atmospheric pressure or an elevated pressure of up to 6 bar and special preference being given to atmospheric pressure.

The reaction time for that reaction is generally from 1 to 60 hours, preferably from 1 to 6 hours.

Compounds of formula II may be prepared, for example, by way of the reaction sequence which follows (see Scheme 2):

Scheme 2:

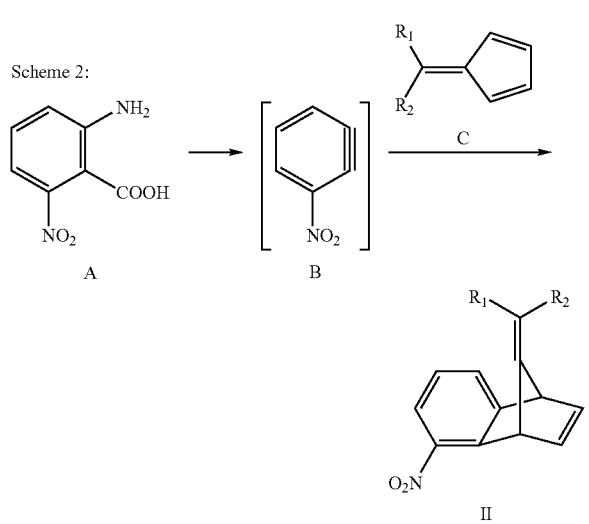

9-Alkylidene-5-nitro-benzonorbornadienes of formula II, wherein $R_1$ and $R_2$ are as defined for formula I, may be prepared by way of a Diels-Alder addition of an in situ-generated dehydrobenzene of formula B [prepared, for example, starting from 6-nitro-anthranilic acid (compound of formula A)] by diazotisation with a $C_{1-8}$alkyl nitrite, such as, for example, iso-amyl nitrite, tert-amyl nitrite, n-amyl nitrite or tert-butyl nitrite, as described in L. Paquette et al., *J. Amer. Chem. Soc.* 99, 3734 (1977), or from other suitable precursors [see H. Pellissier et al., *Tetrahedron*, 59, 701 (2003), R. Muneyuki and H. Tanida, *J. Org. Chem.* 31, 1988 (1966)], to a fulvene of formula C, wherein $R_1$ and $R_2$ are as defined for formula I. That reaction may be carried out in analogy to: R. Muneyuki and H. Tanida, *J. Org. Chem.* 31, 1988 (1966), P. Knochel et al., *Angew. Chem.* 116, 4464 (2004), J. W. Coe et al., *Organic Letters* 6, 1589 (2004), L. Paquette et al, *J. Amer. Chem. Soc.* 99, 3734 (1977), R. N. Warrener et al., *Molecules*, 6, 353 (2001) and R. N. Warrener et al., Molecules, 6, 194 (2001). Suitable aprotic solvents for that step are, for example, diethyl ether, butyl methyl ether, ethyl acetate, dichloromethane, acetone, tetrahydrofuran, toluene, 2-butanone or dimethoxy-ethane. Suitable reaction temperatures are from ambient temperature to 100° C., preferably from 35° C. to 80° C.

Fulvenes of formula C may be prepared according to or in analogous manner to:

M. Neuenschwander et al., *Helv. Chim. Acta*, 54, 1037 (1971), ibid 48, 955 (1965), R. D. Little et al., *J. Org. Chem.* 49, 1849 (1984), 1. Erden et al., *J. Org. Chem.* 60, 813 (1995), S. Collins et al., *J. Org. Chem.* 55, 3395 (1990), J. Thiele, *Chem. Ber.* 33, 666 (1900) and *Liebigs Ann. Chem.* 1, 348 (1906).

Fulvenes of the general formula (C)

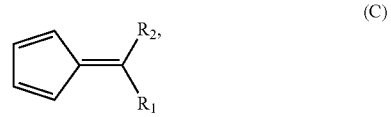

wherein $R_1$ and $R_2$ are as defined for formula I, may be prepared by the reaction of cyclopenta-1,3-diene with a compound of formula (F)

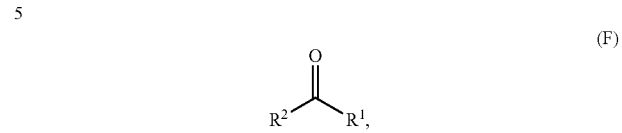

wherein $R^1$ and $R^2$ are as defined for formula I, in the presence of a base.

The reaction for the preparation of compounds of formula (C) is preferably carried out in the presence of an inert solvent. Suitable solvents are, for example, dimethylformamide; dimethyl sulfoxide; N-methyl-2-pyrrolidone; ethers, such as, for example, tetrahydrofuran, tertbutyl methyl ether, diethyl ether, butyl methyl ether, dimethoxyethane; alcohols, such as, for example, $C_1$-$C_{10}$alcohols, such as, for example, methanol or ethanol; or aromatic solvents, such as, for example, toluene, xylene or dichlorobenzene.

Suitable bases are, for example, amine bases, such as, for example, pyrrolidine, morpholine, thiomorpholine or piperidine; alkanolates, such as, for example, sodium methanolate or sodium ethanolate, or hydroxides, such as, for example, KOH or NaOH; preference is given to pyrrolidine.

Suitable amounts of base for the reaction are, for example, from 0.01 to 2 equivalents, especially from 0.25 to 0.8 equivalent.

Temperatures are generally from −20° C. to 80° C., with preference being given to a range from −10° C. to ambient temperature.

The reaction time for that reaction is generally from 30 minutes to 24 hours, preferably from 1 to 6 hours.

EXAMPLE A1

Preparation of 6,6-dimethylfulvene 950 g (5 equivalents) of methanol, 543 g (1.3 equivalents) of acetone and 397 g (6 mol) of cyclopentadiene are mixed together and cooled to −5° C. 107 g (0.25 equivalent) of pyrrolidine are added. The reaction mixture is stirred for 2 hours at −5° C. The reaction is stopped by addition of acetic acid and water. After separation of the phases, the organic phase is extracted with saturated sodium chloride solution. The solvent is removed in vacuo. 535 g of 6,6-dimethylfulvene (purity: 93%; yield: 78%) are obtained.

6-Nitro-anthranilic acid is accessible, for example, in accordance with H. Seidel, *Chem. Ber.* 34, 4351 (1901).
Process Step b):

In one embodiment of the present invention, a single reducing agent is used in Process Step b).

A suitable reducing agent for Process Step b) is, for example, hydrogen in the presence of a metal catalyst.

Suitable amounts of reducing agent for that reaction are, for example, up to 1 equivalent, with preference being given to 1 equivalent for that reaction. Process Step b) is preferably carried out in a closed vessel.

In an embodiment of the process according to the invention in which Process Step b) is carried out in a closed vessel, an excess of hydrogen is, for example, introduced into the reaction mixture in which the metal catalyst is already present. The consumption of hydrogen is then monitored over the course of the reaction time. In that embodiment of the process according to the invention, the reaction is preferably stopped when the desired amount of hydrogen has been consumed.

Suitable metal catalysts are, for example, platinum catalysts, such as, for example, platinum/carbon catalysts (Pt/C) or $PtO_2$; palladium catalysts, such as, for example, Pd/C; rhodium catalysts, such as, for example, Rh/C, $Rh/Al_2O_3$ or $Rh_2O_3$; nickel catalysts, such as, for example, Raney nickel; or iridium catalysts, such as, for example, Ir(COD)Py(Pcy); and mixtures thereof. Special preference is given to Pd/C or Rh/C.

Suitable amounts of metal catalyst for that reaction are, for example, from 0.001 up to 0.5 equivalent, especially from 0.01 up to 0.1 equivalent.

The reaction is preferably carried out in the presence of an inert solvent. Suitable solvents are, for example, alcohols, such as methanol, ethanol, propanol or isopropanol, or aprotic solvents, such as tetrahydrofuran, tert-butyl methyl ether, dioxane, toluene, ethyl acetate or dichloromethane, and mixtures thereof; special preference is given to tetrahydrofuran or methanol.

Temperatures are generally from −40° C. to 80° C., with preference being given to a range from −20° C. to 50° C. and special preference to a range from 0° C. to 30° C. In one embodiment, the temperatures are in a range from 20° C. to 30° C.

The reaction may be carried out at atmospheric pressure or at elevated pressure, with preference being given to atmospheric pressure or an elevated pressure of up to 150 bar and special preference being given to atmospheric pressure or an elevated pressure of up to 100 bar.

The reaction time for that reaction is generally from 1 to 100 hours, preferably from 1 to 24 hours.

Process Step c):

Especially suitable for use in Process Step c) are compounds of formula V wherein Q is chlorine, fluorine, bromine or iodine and $R_3$ is as defined for formula I. More especially suitable are compounds of formula V wherein Q is chlorine, fluorine or bromine and $R_3$ is as defined for formula I. Outstandingly suitable are compounds of formula V wherein Q is chlorine and $R_3$ is as defined for formula I.

In reactions according to the invention with compounds of formula V wherein Q is chlorine, fluorine or bromine and $R_3$ is as defined for formula I (Process Variant c1), compounds of formula V are used in equimolar amount, in less than equimolar amount or in excess in relation to compounds of formula IV, preferably in equimolar amount or in an up to 3-fold excess, especially preferably in equimolar amount or in an up to 1.5-fold excess, very especially preferably in equimolar amount.

The reaction of Process Variant c1) is preferably carried out in the presence of an inert solvent. Suitable solvents are, for example, chlorobenzene, dichloromethane, chloroform, toluene, tetrahydrofuran, diethyl ether, butyl methyl ether or water, and mixtures thereof, with special preference being given to toluene or dichloromethane.

The reaction of Process Variant c1) is preferably carried out in the presence of a base.

Suitable bases are, for example, amine bases, such as, for example, triethylamine or pyridine; or inorganic bases, such as carbonates, e.g. $K_2CO_3$ or $Na_2CO_3$, or hydroxides, e.g. NaOH or KOH; preference is given to trialkylamines and special preference to triethylamine.

Suitable amounts of base for the reaction are, for example, from 1 to 1.5 equivalents, especially from 1 to 1.2 equivalents.

Temperatures are generally from 0° C. to 100° C., with preference being given to a range from 10° C. to 50° C. and special preference to a range from 15° C. to 30° C.

The reaction may be carried out at atmospheric pressure or at elevated pressure, with preference being given to atmospheric pressure.

The reaction time for that reaction is generally from 1 to 48 hours, preferably from 1 to 24 hours.

Also especially suitable for use in Process Step c) are compounds of formula V wherein Q is hydroxy and $R_3$ is as defined for formula I.

In reactions according to the invention with compounds of formula V wherein Q is hydroxy and $R_3$ is as defined for formula I (Process Variant c2), compounds of formula V are used in equimolar amount, in less than equimolar amount or in excess in relation to compounds of formula IV, preferably in equimolar amount or in an up to 3-fold excess, especially preferably in equimolar amount or in an up to 1.5-fold excess, very especially preferably in equimolar amount.

The reactions according to the invention of Process Variant c2), that is, with compounds of formula V wherein Q is hydroxy and $R_3$ is as defined for formula I, are preferably carried out in the presence of an activating agent.

A suitable activating agent is, for example, bis(2-oxo-3-oxazolidinyl)-phosphinic acid chloride.

The reaction of Process Variant c2) is preferably carried out in the presence of an inert solvent. Suitable inert solvents are, for example, dichloromethane and chloroform, and mixtures thereof; dichloromethane is especially preferred.

The reaction of Process Variant c2) is preferably carried out in the presence of a base.

Suitable bases are, for example, amine bases, such as, for example, triethylamine or pyridine; triethylamine is especially preferred.

Suitable amounts of base for the reaction are, for example, at least 2 equivalents, especially from 2 up to 3 equivalents.

Temperatures are generally from 0° C. to 100° C., preference being given to a range from 10° C. to 50° C. and special preference to a range from 15° C. to 30° C.

The reaction may be carried out at atmospheric pressure or at elevated pressure, with preference being given to atmospheric pressure.

The reaction time for that reaction is generally from 1 to 48 hours, preferably from 1 to 24 hours.

Also suitable for use in Process Step c) are compounds of formula V wherein Q is $C_1$-$C_6$-alkoxy and $R_3$ is as defined for formula I.

Especially suitable are compounds of formula V wherein Q is methoxy or ethoxy and $R_3$ is as defined for formula I.

In reactions according to the invention with compounds of formula V wherein Q is $C_1$-$C_6$-alkoxy and $R_3$ is as defined for formula I (Process Variant c3), compounds of formula V are used in equimolar amount, in less than equimolar amount or in excess in relation to compounds of formula IV.

The reaction of Process Variant c3) may be carried out in the presence of an inert solvent. Suitable solvents are, for example, chlorobenzene, dichloromethane, chloroform, toluene, tetrahydrofuran, diethyl ether or butyl methyl ether, and mixtures thereof; chlorobenzene or toluene is preferred as solvent.

The reaction may also be carried out in the absence of a solvent.

The reaction of Process Variant c3) is preferably carried out in the presence of a base.

Suitable bases are, for example, amine bases, such as, for example, triethylamine or pyridine; inorganic bases, such as carbonates, e.g. $K_2CO_3$ or $Na_2CO_3$, or hydroxides, e.g. NaOH or KOH; or alkoxides, such as, for example, potassium tert-butoxide. Preference is given, for example, to potassium tertbutoxide.

Suitable amounts of base for the reaction are, for example, from 1 to 1.5 equivalents, especially from 1 to 1.2 equivalents.

Temperatures are generally from 0° C. to 120° C., with preference being given to a range from 50° C. to 100° C. and special preference to a range from 70° C. to 100° C.

The reaction may be carried out at atmospheric pressure or at elevated pressure, with preference being given to atmospheric pressure.

The reaction time for that reaction is generally from 1 to 48 hours, preferably from 1 to 24 hours.

Compounds of formula V are described in WO 04/035589 or may be prepared by way of the processes described therein.

A preferred embodiment of the process according to the invention is a process for the preparation of compounds of formula I wherein $R_1$ and $R_2$ are methyl and $R_3$ is $CF_2H$ which comprises a) reacting a compound of formula II wherein $R_1$ and $R_2$ are methyl with hydrogen, in the presence of a rhodium/carbon catalyst, to form a compound of formula III wherein $R_1$ and $R_2$ are methyl, tetrahydrofuran being used as solvent; and (b) reacting that compound with hydrogen in the presence of a Raney nickel catalyst to form a compound of formula IV wherein $R_1$ and $R_2$ are methyl, tetrahydrofuran being used as solvent; and (c) converting that compound into the compound of formula I by reaction with a compound of formula V wherein 0 is hydroxy and $R_3$ is $CF_2H$, in the presence of bis(2-oxo-3-oxazolidinyl)-phosphinic acid chloride, dichloromethane being used as solvent and the reaction being carried out in the presence of triethylamine.

By selecting suitable reaction conditions for Reaction Step a), the compound of formula III obtained in Reaction Step a) can be converted to a compound of formula IV directly, without isolation of intermediates, by complete hydrogenation. That preferred embodiment of the present invention is a particular advantage of the process according to the invention.

In that preferred embodiment, more preferably a total of 5 equivalents of reducing agent is used in the Reaction Steps a) and b) combined.

In that preferred embodiment of the present invention, hydrogen in the presence of a metal catalyst is preferably used as reducing agent in Reaction Step a) and Reaction Step b).

In that preferred embodiment of the present invention, the same metal catalyst is preferably used in Reaction Step a) and Reaction Step b).

Suitable amounts of metal catalyst for that preferred embodiment are, for example, from 0.001 to 0.5 equivalent, especially from 0.01 to 0.1 equivalent.

Preferably, the combination of the Reaction Steps a) and b) in that preferred embodiment of the process according to the invention is carried out in a closed vessel. In that combination, an excess of hydrogen is, for example, introduced into the reaction mixture in which the metal catalyst is already present. The consumption of hydrogen is then monitored over the course of the reaction time. In that preferred embodiment of the process according to the invention, the reaction is preferably stopped when the desired amount of hydrogen, which is more preferably 5 equivalents, has been consumed.

In that embodiment, the reaction may be carried out at atmospheric pressure or at an elevated pressure of up to 150 bar, with preference being given to atmospheric pressure or an elevated pressure of up to 50 bar, special preference being given to atmospheric pressure or an elevated pressure of up to 20 bar, and very special preference being given to atmospheric pressure or an elevated pressure of up to 6 bar.

The reaction time of that preferred embodiment of the reaction is generally from 1 to 100 hours, preferably from 1 to 24 hours.

The present invention is explained in greater detail by way of the following Examples:

EXAMPLE P1

Preparation of
9-isopropylidene-5-amino-benzonorbornene
(Compound No. Z2.11)

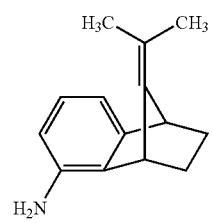

5.0 g of 9-isopropylidene-5-nitro-benzonorbornadiene (Comp. No. Z1.11) (22 mmol) are hydrogenated in 50 ml of tetrahydrofuran in the presence of 1.5 g of 5% Rh/C at 25° C. and atmospheric pressure. After the absorption of 4 equivalents of hydrogen (2.01 liters or 102% of theory) the mixture is filtered, the solvent is removed in vacuo and the residue is purified by chromatography on a silica gel column using hexane/ethyl acetate (6:1) as eluant. 2.76 g of 9-isopropylidene-5-amino-benzonorbornene are obtained in the form of a solid (m.p. 81-82° C.; yield: 62.9% of theory). $^1$H-NMR (CDCl$_3$), ppm: 6.90 (t, 1H), 6.67 (d, 1H), 6.46 (d, 1H), 3.77 (m, 1H), 3.73 (m, 1H), 3.35 (brd, exchangeable with D$_2$O, 2H), 1.89 (m, 2H), 1.63 (2 s, 6H), 1.26 (m, 2H). $^{13}$C-NMR (CDCl$_3$), ppm: 148.73, 147.65, 138.30, 131.75, 126.19, 113.12, 110.89, 110.19, 43.97, 39.44, 26.98, 26.06, 19.85, 19.75.

EXAMPLE P2

Preparation of
9-isopropylidene-5-amino-benzonorbornene
(Compound No. Z2.11)

In a 1-liter steel autoclave, 5% rhodium on active carbon (43.1 g, water-moist, water content 70%) are added to 225 g of methanol. A hydrogen pressure of 7 bar is applied and stirring is carried out at ambient temperature. In the course of 2 hours, a solution of 96.7 g of 9-isopropylidene-5-nitro-1,4-dihydro-1,4-methano-naphthalene in 120 g of tetrahydrofuran and 24 g of methanol is added to that mixture. In parallel, hydrogen is taken up at a pressure of 7 bar. The reaction is stopped 30 minutes after the end of the addition. The reaction mixture is filtered through cellulose and washed with methanol. The filtrate is concentrated to dryness by evaporation. Methanol is added to the residue obtained. The precipitated crude product is filtered off and concentrated to dryness by evaporation. The residue is chromatographed on silica gel using ethyl acetate/hexane (1:6). 9-Isopropylidene-5-amino-benzonorbornene is obtained.

EXAMPLE P3

Preparation of 9-isopropyl-5-amino-benzonorbornene (Comp. No. Z3.11)

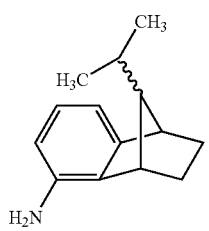

0.2 g of 9-isopropylidene-5-amino-benzonorbornene (Z2.11) is hydrogenated for 24 hours in 40 ml of tetrahydrofuran in the presence of 0.1 g of RaNi (EtOH-treated) at 25° C. and 100 bar pressure. The mixture is filtered, the solvent removed in vacuo, and the residue purified by chromatography on a silica gel column using hexane/ethyl acetate (6:1) as eluant. 9-Isopropyl-5-amino-benzonorbornene (Z3.11) is obtained in the form of a solid (syn/anti ratio 29:71; yield: 82% of theory).

EXAMPLE P4

Preparation of 9-isopropyl-5-amino-benzonorbornene (Comp. No. Z3.11)

41.4 g of 9-isopropylidene-5-nitro-benzonorbornadiene (Comp. No. Z1.11) in 1 liter of tetrahydrofuran are hydrogenated exhaustively in the presence of 22 g of 5% Pd/C at 25° C. under normal pressure for 4 hours. The reaction mixture is filtered, the solvent is removed in vacuo and purification by chromatography on silica gel is carried out using ethyl acetate/hexane (1:7) as eluant. 29.9 g of 9-isopropyl-5-amino-benzonorbornene (Comp. No. Z3.11) (syn/anti ratio 32:68; yield: 81.5% of theory) are obtained in the form of an oil. Syn epimer: $^1$H-NMR (CDCl$_3$), ppm: 6.91 (t, 1H), 6.64 (d, 1H), 6.48 (d, 1H), 3.54 (brd, exchangeable with D$_2$O, 2H), 3.20 (m, 1H), 3.15 (m, 1H), 1.92 (m, 2H), 1.53 (d, 1H), 1.18 (m, 2H), 1.02 (m, 1H), 0.81 (m, 6H); $^{13}$C-NMR (CDCl$_3$), ppm: 147.73, 140.03, 130.15, 126.41, 113.35, 112.68, 69.00, 46.62, 42.06, 27.74, 26.83, 25.45, 22.32, 22.04; anti epimer: $^1$H-NMR (CDCl$_3$), ppm: 6.89 (t, 1H), 6.63 (d, 1H), 6.46 (d, 1H), 3.55 (brd, exchangeable with D$_2$O, 2H), 3.16 (m, 1H), 3.13 (m, 1H), 1.87 (m, 2H), 1.48 (d, 1H), 1.42 (m, 1H), 1.12 (m, 2H), 0.90 (m, 6H); $^{13}$C-NMR (CDCl$_3$), ppm: 150.72, 138.74, 133.63, 126.15, 112.94, 111.53, 68.05, 45.21, 40.61, 26.25, 24.47, 23.55, 20.91 (2×). The syn/anti assignments are made on the basis of NOE-NMR experiments.

EXAMPLE P5

Preparation of 3-difluoromethyl-1-methyl-1H-pyrazole-4-carboxylic acid (9-isopropyl-1,2,3,4-tetrahydro-1,4-methano-naphthalen-5-yl)-amide (Comp. No. A.11)

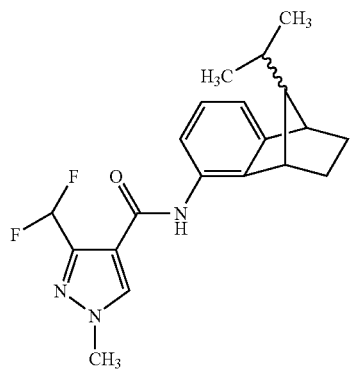

1.9 g of bis(2-oxo-3-oxazolidinyl)-phosphinic acid chloride (7.2 mmol, 1.4 equivalents) are added at ambient temperature to a solution of 1 g of 9-isopropyl-5-amino-benzonorbornene (Comp. No. Z3.11, syn/anti ratio 90:10; 5 mmol), 1.7 ml of triethylamine (12.1 mmol, 2.4 equivalents) and 1.2 g of 3-difluoromethyl-1-methyl-1H-pyrazole-4-carboxylic acid (6.2 mmol, 1.4 equivalents) in 40 ml of dichloromethane and stirring is carried out for 20 hours. After the addition of water and saturated NaHCO$_3$ solution, the organic phase is extracted with ethyl acetate. Purification on silica gel in ethyl acetate/hexane (2:3) and subsequent crystallisation from hexane yields 1.31 g of 3-difluoromethyl-1-methyl-1H-pyrazole-4-carboxylic acid (9-isopropyl-1,2,3,4-tetrahydro-1,4-methano-naphthalen-5-yl)-amide (m.p. 124-125° C.; syn/anti ratio 92:8 according to $^1$H-NMR; yield: 73%). The crystalline material was analyzed by differential scanning calorimetry and x-ray diffraction and was identified as crystal modification B of syn-3-difluoromethyl-1-methyl-1H-pyrazole-4-carboxylic acid (9-isopropyl-1,2,3,4-tetrahydro-1,4-methano-naphthalen-5-yl)-amide (see FIG. 7).

EXAMPLE P6

Preparation of 3-difluoromethyl-1-methyl-1H-pyrazole-4-carboxylic acid (9-isopropyl-1,2,3,4-tetrahydro-1,4-methano-naphthalen-5-yl)-amide (Comp. No. A.11)

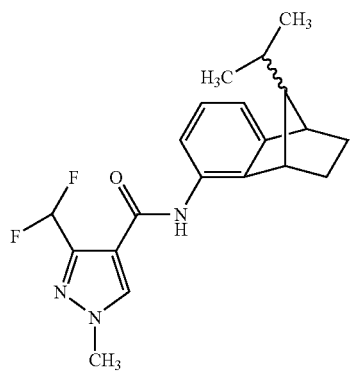

To a solution of 100 g of 9-isopropyl-5-amino-benzonorbornene (Comp. No. Z3.11, syn/anti ratio 90:10; 0.5 mol, 50% chlorobenzene solution) and 55.7 g of triethylamine (0.55 mol, 1.1 equivalents) in 200 g of chlorobenzene there are added at 40° C., in the course of 2 hours, 97.3 g of 3-difluoromethyl-1-methyl-1H-pyrazole-4-carbonyl chloride (50% chlorobenzene solution, 0.5 mol, 1 equivalent) and stirring is carried out for 1 hour. After the addition of water and hydrochloric acid (a pH of 6-7 is established), the organic phase is extracted with chlorobenzene. The organic phase is concentrated by distilling off chlorobenzene. Following subsequent crystallisation from methanol/water (3:1 mixture), 126 g of 3-difluoromethyl-1-methyl-1H-pyrazole-4-carboxylic acid (9-isopropyl-1,2,3,4-tetrahydro-1,4-methano-naphthalen-5-yl)-amide are obtained (m.p. 124-125° C.; purity: 99.2%; syn/anti ratio 95:5 according to GC, yield: 70%). The crystalline material was analyzed by differential scanning calorimetry and x-ray diffraction and was identified as crystal modification B of syn-3-difluoromethyl-1-methyl-1H-pyrazole-4-carboxylic acid (9-isopropyl-1,2,3,4-tetrahydro-1,4-methano-naphthalen-5-yl)-amide (see FIG. 8.

EXAMPLE P7

Preparation of
9-isopropylidene-5-nitro-benzonorbornadiene

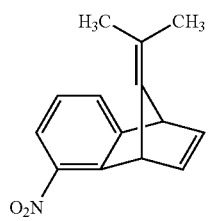

A mixture of 110.4 g of 6-nitroanthranilic acid (0.6 mol) and 98.5 g of 6,6-dimethylfulvene (1.5 equivalents) in 700 ml of dimethoxyethane are added dropwise at 72° C. to a solution of 96.3 g of tert-butyl nitrite (1.4 equivalents) in 2 liters of 1,2-dimethoxyethane under a nitrogen atmosphere. Evolution of gas commences and the temperature of the mixture rises to 79° C. The evolution of gas subsides after 30 minutes. After stirring for 3 hours at the reflux temperature of the solvent, the mixture is cooled to ambient temperature. The solvent is removed in vacuo and the residue is purified by chromatography on a silica gel column using hexane/ethyl acetate (95:5) as eluant. 76.7 g of 9-isopropylidene-5-nitro-benzonorbornadiene are obtained in the form of a yellow solid (m.p. 94-95° C.). $^1$H-NMR (CDCl$_3$), ppm: 7.70 (d, 1H), 7.43 (d, 1H), 7.06 (t, 1H), 6.99 (m, 2H), 5.34 (brd s, 1H), 4.47 (brd s, 1H), 1.57 (2 d, 6H). $^{13}$C-NMR (CDCl$_3$), ppm: 159.83, 154.30, 147.33, 144.12, 142.89, 141.93, 125.23 (2×), 119.32, 105.68, 50.51, 50.44, 19.05, 18.90.

EXAMPLE P8

Preparation of
9-isopropylidene-5-nitro-benzonorbornadiene

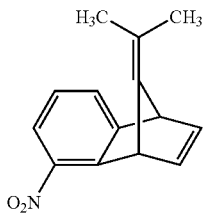

98.5 g of 6,6-dimethylfulvene in 500 g of methyl ethyl ketone are heated to 60° C. A solution of 182 g of 6-nitroanthranilic acid in 700 g of methyl ethyl ketone are added over a period of 2 hours at 60° C. under a nitrogen atmosphere, and in parallel 216 g of tert-amyl nitrite are added in the course of 2.5 hours. The solvent is removed in vacuo at 60° C. 200 g of xylene are added, and then 1200 g of hexane are added. The suspension obtained is filtered and washed with hexane. The solvent is removed in vacuo at 60° C., and 200 g of methanol are added to the crude product. The crude product that crystallises out is filtered off at 0° C. and washed with 100 g of methanol. After removal of the residual solvent in vacuo at 60° C., 120 g of 9-isopropylidene-5-nitro-benzonorbornadiene (m.p. 93° C.) are obtained.

EXAMPLE P9

Preparation of 9-isopropylidene-
5-amino-benzonorbornadiene (Comp. No. Z4.11)

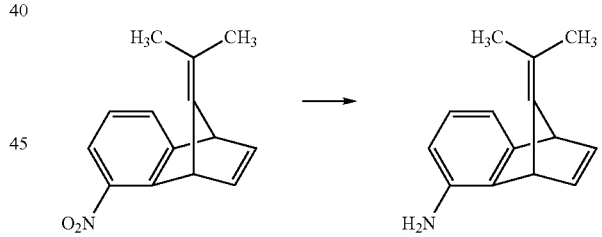

Powdered iron is added to 2.72 g of 9-isopropylidene-5-nitro-benzonorbornadiene (Comp. No. Z1.11) dissolved in 50 ml of tetrahydrofuran and 61 ml of acetic acid (5% in water) and stirring is carried out for 20 hours at 30° C. The crude product is filtered off and ethyl acetate is added. Washing is then carried out with aqueous NaHCO$_3$ solution and saturated sodium chloride solution, and drying is carried out by addition of Na$_2$SO$_4$. The crude product is purified on a silica gel column (eluant: 1:3 ethyl acetate:hexane). 2.01 g of 9-isopropylidene-5-amino-benzonorbornadiene are obtained in the form of beige crystals (yield: 85%; m.p. 121-123° C.).

$^1$H-NMR (CDCl$_3$): 6.95 (m, 2H), 6.80 (m, 2H), 6.39 (d, 1H), 4.41 (m, 1H), 4.37 (m, 1H), 3.91 (brd, exchangeable with D$_2$O, 2H), 1.58 (s, 3H), 1.57 (s, 3H); $^{13}$C-NMR (CDCl$_3$): 160.8, 151.6, 143.0, 141.9, 139.1, 134.2, 125.3, 113.2, 112.5, 101.5, 50.9, 46.3, 19.0, 18.8.

P10

Preparation of 3-difluoromethyl-1-methyl-1H-pyrazole-4-carboxylic acid (9-isopropyl-1,2,3,4-tetrahydro-1,4-methano-naphthalen-5-yl)-amide (Comp. No. A.11)

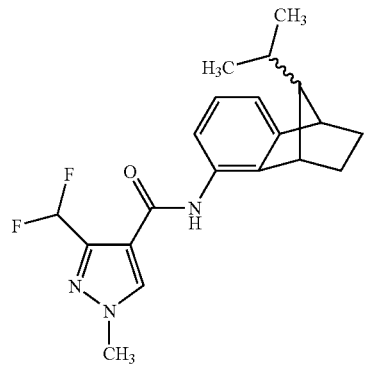

6.2 g of 9-isopropyl-5-amino-benzonorbornene (Comp. No. Z3.11, syn/anti ratio 90:10; 30 mmol, 1.05 equivalents) and 1.6 g of potassium tert-butoxide (14.7 mmol, 0.5 equivalent) are added to a solution of 6 g of 3-difluoromethyl-1-methyl-1H-pyrazole-4-carboxylic acid ethyl ester (29 mmol) in 60 ml of chlorobenzene. The reaction mixture is heated to 95° C. and the chlorobenzene solvent is completely removed in vacuo. The reaction mixture is heated to 120° C. and stirred for 20 hours. 30 ml of chlorobenzene are then added. The organic phase is extracted twice with water, first at low pH, then at high pH. The organic phase is concentrated by distilling off chlorobenzene. 8 g of 3-difluoromethyl-1-methyl-1H-pyrazole-4-carboxylic acid (9-isopropyl-1,2,3,4-tetrahydro-1,4-methano-naphthalen-5-yl)-amide are obtained in the form of a brown oil (crude yield: 33%).

The preparation of starting compounds of formula V is described by the following Example.

EXAMPLE A2

Preparation of 3-difluoromethyl-1-methyl-1H-pyrazole-4-carbonyl chloride

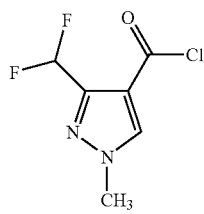

69.5 g of thionyl chloride (0.58 mol, 1.17 equivalents) are added at 110° C. in the course of 2 hours to a solution of 88 g of 3-difluoromethyl-1-methyl-1H-pyrazole-4-carboxylic acid (0.5 mol) in 440 g of chlorobenzene. The reaction mixture is stirred for 1 hour at 110° C. The reaction mixture is concentrated to a crude product solution. 190 g of 3-difluoromethyl-1-methyl-1H-pyrazole-4-carbonyl chloride (50% in chlorobenzene, yield: 98%) is obtained. The crude product solution is used without being further purified.

The following compounds of formula I may be prepared on the basis of the above Examples:

TABLE 1

Compounds of formula I

| Comp. No. | $R_1$ | $R_2$ | $R_3$ | Remarks |
|---|---|---|---|---|
| A.01 | H | $CH_3$ | $CF_2H$ | syn/anti mixture |
| A.02 | H | $C_2H_5$ | $CF_2H$ | syn/anti mixture |
| A.03 | H | $n\text{-}C_3H_7$ | $CF_2H$ | syn/anti mixture |
| A.04 | H | $i\text{-}C_3H_7$ | $CF_2H$ | syn/anti mixture |
| A.05 | $C_2H_5$ | $i\text{-}C_3H_7$ | $CF_2H$ | syn/anti mixture |
| A.06 | H | $n\text{-}C_4H_9$ | $CF_2H$ | syn/anti mixture |
| A.07 | H | $i\text{-}C_4H_9$ | $CF_2H$ | syn/anti mixture |
| A.08 | H | $sec\text{-}C_4H_9$ | $CF_2H$ | syn/anti mixture |
| A.09 | H | $t\text{-}C_4H_9$ | $CF_2H$ | syn/anti mixture |
| A.10 | H | $n\text{-}C_5H_{11}$ | $CF_2H$ | syn/anti mixture |
| A.11 | $CH_3$ | $CH_3$ | $CF_2H$ | syn/anti mixture |
| A.12 | $C_2H_5$ | $C_2H_5$ | $CF_2H$ | syn/anti mixture |
| A.13 | $CH_3$ | $C_2H_5$ | $CF_2H$ | syn/anti mixture |
| A.14 | $CH_3$ | $n\text{-}C_3H_7$ | $CF_2H$ | syn/anti mixture |
| A.15 | $CH_3$ | $i\text{-}C_3H_7$ | $CF_2H$ | syn/anti mixture |
| A.16 | $C_2H_5$ | $i\text{-}C_3H_7$ | $CF_2H$ | syn/anti mixture |
| A.17 | H | H | $CF_2H$ | syn/anti mixture |
| A.18 | H | $CH_3$ | $CF_3$ | syn/anti mixture |
| A.19 | H | $C_2H_5$ | $CF_3$ | syn/anti mixture |
| A.20 | H | $n\text{-}C_3H_7$ | $CF_3$ | syn/anti mixture |
| A.21 | H | $i\text{-}C_3H_7$ | $CF_3$ | syn/anti mixture |
| A.22 | $C_2H_5$ | $i\text{-}C_3H_7$ | $CF_3$ | syn/anti mixture |
| A.23 | H | $n\text{-}C_4H_9$ | $CF_3$ | syn/anti mixture |
| A.24 | H | $i\text{-}C_4H_9$ | $CF_3$ | syn/anti mixture |
| A.25 | H | $sec\text{-}C_4H_9$ | $CF_3$ | syn/anti mixture |
| A.26 | H | $t\text{-}C_4H_9$ | $CF_3$ | syn/anti mixture |
| A.27 | H | $n\text{-}C_5H_{11}$ | $CF_3$ | syn/anti mixture |
| A.28 | $CH_3$ | $CH_3$ | $CF_3$ | syn/anti mixture |
| A.29 | $C_2H_5$ | $C_2H_5$ | $CF_3$ | syn/anti mixture |
| A.30 | $CH_3$ | $C_2H_5$ | $CF_3$ | syn/anti mixture |
| A.31 | $CH_3$ | $n\text{-}C_3H_7$ | $CF_3$ | syn/anti mixture |
| A.32 | $CH_3$ | $i\text{-}C_3H_7$ | $CF_3$ | syn/anti mixture |
| A.33 | $C_2H_5$ | $i\text{-}C_3H_7$ | $CF_3$ | syn/anti mixture |
| A.34 | H | H | $CF_3$ | syn/anti mixture |

Preferred compounds of formula II are listed in the following Table:

TABLE 2

Compounds of formula II

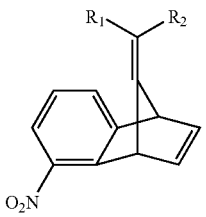

(II)

| Comp. No. | R$_1$ | R$_2$ | Remarks |
|---|---|---|---|
| Z1.01 | H | CH$_3$ | E/Z mixture |
| Z1.02 | H | C$_2$H$_5$ | E/Z mixture |
| Z1.03 | H | n-C$_3$H$_7$ | E/Z mixture |
| Z1.04 | H | i-C$_3$H$_7$ | E/Z mixture |
| Z1.05 | C$_2$H$_5$ | i-C$_3$H$_7$ | E/Z mixture |
| Z1.06 | H | n-C$_4$H$_9$ | E/Z mixture |
| Z1.07 | H | i-C$_4$H$_9$ | E/Z mixture |
| Z1.08 | H | sec-C$_4$H$_9$ | E/Z mixture |
| Z1.09 | H | t-C$_4$H$_9$ | E/Z mixture |
| Z1.10 | H | n-C$_5$H$_{11}$ | E/Z mixture |
| Z1.11 | CH$_3$ | CH$_3$ | |
| Z1.12 | C$_2$H$_5$ | C$_2$H$_5$ | |
| Z1.13 | CH$_3$ | C$_2$H$_5$ | E/Z mixture |
| Z1.14 | CH$_3$ | n-C$_3$H$_7$ | E/Z mixture |
| Z1.15 | CH$_3$ | i-C$_3$H$_7$ | E/Z mixture |
| Z1.16 | C$_2$H$_5$ | i-C$_3$H$_7$ | E/Z mixture |
| Z1.17 | H | H | |

Preferred compounds of formula III are listed in the following Table:

TABLE 3

Compounds of formula III

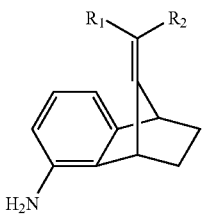

(III)

| Comp. No. | R$_1$ | R$_2$ | Remarks |
|---|---|---|---|
| Z2.01 | H | CH$_3$ | E/Z mixture |
| Z2.02 | H | C$_2$H$_5$ | E/Z mixture |
| Z2.03 | H | n-C$_3$H$_7$ | E/Z mixture |
| Z2.04 | H | i-C$_3$H$_7$ | E/Z mixture |
| Z2.05 | C$_2$H$_5$ | i-C$_3$H$_7$ | E/Z mixture |
| Z2.06 | H | n-C$_4$H$_9$ | E/Z mixture |
| Z2.07 | H | i-C$_4$H$_9$ | E/Z mixture |
| Z2.08 | H | sec-C$_4$H$_9$ | E/Z mixture |
| Z2.09 | H | t-C$_4$H$_9$ | E/Z mixture |
| Z2.10 | H | n-C$_5$H$_{11}$ | E/Z mixture |
| Z2.11 | CH$_3$ | CH$_3$ | |
| Z2.12 | C$_2$H$_5$ | C$_2$H$_5$ | |
| Z2.13 | CH$_3$ | C$_2$H$_5$ | E/Z mixture |
| Z2.14 | CH$_3$ | n-C$_3$H$_7$ | E/Z mixture |
| Z2.15 | CH$_3$ | i-C$_3$H$_7$ | E/Z mixture |
| Z2.16 | C$_2$H$_5$ | i-C$_3$H$_7$ | E/Z mixture |
| Z2.17 | H | H | |

Preferred compounds of formula IV are listed in the following Table:

TABLE 4

Compounds of formula IV

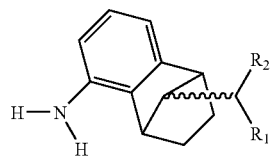

(IV)

| Comp. No. | R$_1$ | R$_2$ | Remarks |
|---|---|---|---|
| Z3.01 | H | CH$_3$ | syn/anti mixture |
| Z3.02 | H | C$_2$H$_5$ | syn/anti mixture |
| Z3.03 | H | n-C$_3$H$_7$ | syn/anti mixture |
| Z3.04 | H | i-C$_3$H$_7$ | syn/anti mixture |
| Z3.05 | C$_2$H$_5$ | i-C$_3$H$_7$ | syn/anti mixture |
| Z3.06 | H | n-C$_4$H$_9$ | syn/anti mixture |
| Z3.07 | H | i-C$_4$H$_9$ | syn/anti mixture |
| Z3.08 | H | sec-C$_4$H$_9$ | syn/anti mixture |
| Z3.09 | H | t-C$_4$H$_9$ | syn/anti mixture |
| Z3.10 | H | n-C$_5$H$_{11}$ | syn/anti mixture |
| Z3.11 | CH$_3$ | CH$_3$ | syn/anti mixture |
| Z3.12 | C$_2$H$_5$ | C$_2$H$_5$ | syn/anti mixture |
| Z3.13 | CH$_3$ | C$_2$H$_5$ | syn/anti mixture |
| Z3.14 | CH$_3$ | n-C$_3$H$_7$ | syn/anti mixture |
| Z3.15 | CH$_3$ | i-C$_3$H$_7$ | syn/anti mixture |
| Z3.16 | C$_2$H$_5$ | i-C$_3$H$_7$ | syn/anti mixture |
| Z3.17 | H | H | syn/anti mixture |

Preferred compounds of formula IIA are listed in the following Table:

TABLE 5

Compounds of formula IIA

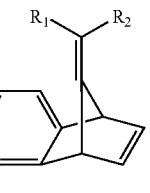

(IIA)

| Comp. No. | R$_1$ | R$_2$ | Remarks |
|---|---|---|---|
| Z4.01 | H | CH$_3$ | E/Z mixture |
| Z4.02 | H | C$_2$H$_5$ | E/Z mixture |
| Z4.03 | H | n-C$_3$H$_7$ | E/Z mixture |
| Z4.04 | H | i-C$_3$H$_7$ | E/Z mixture |
| Z4.05 | C$_2$H$_5$ | i-C$_3$H$_7$ | E/Z mixture |
| Z4.06 | H | n-C$_4$H$_9$ | E/Z mixture |
| Z4.07 | H | i-C$_4$H$_9$ | E/Z mixture |
| Z4.08 | H | sec-C$_4$H$_9$ | E/Z mixture |
| Z4.09 | H | t-C$_4$H$_9$ | E/Z mixture |
| Z4.10 | H | n-C$_5$H$_{11}$ | E/Z mixture |
| Z4.11 | CH$_3$ | CH$_3$ | |
| Z4.12 | C$_2$H$_5$ | C$_2$H$_5$ | |
| Z4.13 | CH$_3$ | C$_2$H$_5$ | E/Z mixture |
| Z4.14 | CH$_3$ | n-C$_3$H$_7$ | E/Z mixture |
| Z4.15 | CH$_3$ | i-C$_3$H$_7$ | E/Z mixture |
| Z4.16 | C$_2$H$_5$ | i-C$_3$H$_7$ | E/Z mixture |
| Z4.17 | H | H | |

The starting materials for the process of the present invention are distinguished by ease of availability and good handling properties and are moreover reasonably priced.

In an especially preferred embodiment (bb) of the present invention, the reducing agent used in Step (b) is hydrogen in the presence of a rhodium catalyst.

That especially preferred embodiment (bb) makes it possible to prepare in simple manner compounds of formula I in which the ratio of syn isomers of formula Ia to anti isomers of formula Ib is significantly higher than that described in WO 04/035589; generally, syn/anti ratios of the prepared 9-monosubstituted pyrazolyl-4-carboxylic acid benzonorbornen-5-yl-amides of more than 90:10 are achieved.

The reaction sequence described in WO 04/035589 (Scheme 1) yields a syn:anti ratio of 9-monosubstituted pyrazolyl-4-carboxylic acid benzonorbornene fungicides in favour of the anti isomer. Working up of the individual syn/anti isomers in accordance with the state of the art is generally carried out using customary methods, such as, for example, chromatographic methods.

In contrast thereto, according to the especially preferred embodiment (bb) of the present process there are prepared, in simple manner, compounds of formula I wherein the ratio of compounds of formula Ia (syn) to compounds of formula Ib (anti) is from 90:10 to 99:1.

It is therefore a particular advantage of the especially preferred embodiment (bb) of the present process that mixtures of compounds of formula I can be prepared in simple manner that have a syn/anti ratio strongly in favour of the syn isomer.

In the context of the present invention, a "mixture of compounds of formula I that has a syn/anti ratio strongly in favour of the syn isomer" is understood to be a mixture of compounds of formula I wherein the ratio of compounds of formula Ia (syn) to compounds of formula Ib (anti) is from 90:10 to 99:1.

In the process according to the invention, the syn/anti proportion of the end products of the process, the 9-monosubstituted pyrazolyl-4-carboxylic acid benzonorbornen-5-yl-amides of formula I, is substantially determined by the syn/anti proportion of the 5-amino-benzo-norbornenesk of formula IV formed when Process Step (b) is carried out.

On carrying out Process Step (c), the amidation of the 5-amino-benzonorbornenes to form the end products of the process, the compounds of formula I, the syn proportion remains substantially unchanged.

After carrying out Process Step (c), the syn proportion of the compounds of formula I can be increased by means of fractional crystallisation using suitable solvents, for example using a tert-butyl methyl ether/hexane mixture or methanol as solvent.

In that especially preferred embodiment (bb) of the process according to the invention, the compounds of formula III obtained according to Process Step (a)

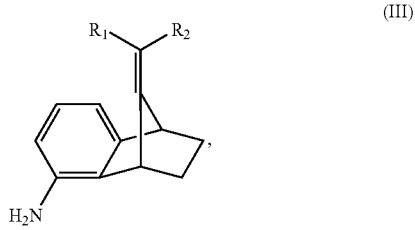

(III)

wherein $R_1$ and $R_2$ are as defined for formula I, are reacted bb) with hydrogen in the presence of a rhodium catalyst to form a compound of formula IV

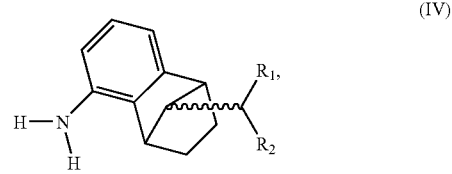

(IV)

wherein $R_1$ and $R_2$ are as defined for formula I and wherein the ratio of compounds of formula IVa (syn) to compounds of formula IVb (anti) is more than 90:10. Those compounds are then used in Process Step (c).

After carrying out Process Step (c), the syn proportion is substantially unchanged. That especially preferred process variant accordingly results in compounds of formula I wherein the ratio of compounds of formula Ia (syn) to compounds of formula Ib (anti) is more than 90:10.

Process Step bb):

Suitable rhodium catalysts are, for example, Rh/C, $RhAl_2O_3$ or $Rh_2O_3$ and mixtures thereof. Special preference is given to Rh/C.

The reaction is preferably carried out in the presence of an inert solvent. Suitable solvents are, for example, alcohols, such as methanol, ethanol, propanol or isopropanol, or aprotic solvents, such as tetrahydrofuran, tert-butyl methyl ether, ethyl acetate, dioxane or toluene, and mixtures thereof; special preference is given to ethanol or methanol.

The temperatures are generally from 0° C. to 80° C., with preference being given to a range from 0° C. to 25° C.

The reaction time for that reaction is generally from 1 to 100 hours, preferably from 1 to 24 hours.

Also, in the especially preferred embodiment (bb) of the present invention, by selecting suitable reaction conditions for Reaction Step a), the compound of formula III obtained in Reaction Step a) can be reacted to form a compound of formula IV directly, without isolation of intermediates, by complete hydrogenation. That very especially preferred embodiment of the present invention is a very special advantage of the process according to the invention. In that preferred arrangement of the embodiment (bb), a total of 5 equivalents of reducing agent is preferably used in Reaction Steps a) and b) combined.

In that preferred arrangement of the embodiment (bb), the same metal catalyst is preferably used in Reaction Step a) and Reaction Step b).

Suitable amounts of metal catalyst for that preferred arrangement of embodiment (bb) are, for example, from 0.001 up to 0.5 equivalent, especially from 0.01 up to 0.1 equivalent.

The combination of Reaction steps a) and b) in that preferred arrangement of the embodiment (bb) is preferably carried out in a closed vessel. In that arrangement an excess of hydrogen is, for example, introduced into the reaction mixture in which the metal catalyst is already present. The consumption of hydrogen is then monitored over the course of the reaction time. In that preferred arrangement of embodiment (bb), the reaction is preferably stopped when the desired amount of hydrogen, which is more preferably 5 equivalents, has been consumed.

In that preferred arrangement of embodiment (bb), the reaction may be carried out at atmospheric pressure or at an elevated pressure of up to 150 bar, with preference being given to atmospheric pressure or an elevated pressure of up to 50 bar, special preference being given to atmospheric pressure or an elevated pressure of up to 20 bar, and very special preference being given to atmospheric pressure or an elevated pressure of up to 6 bar.

The reaction time of that preferred embodiment of the reaction is generally from 1 to 100 hours, preferably from 1 to 24 hours The above-described especially preferred embodiment (bb) of the process according to the invention is explained in greater detail by way of the following Example:

EXAMPLE P11

Preparation of 9-isopropyl-5-amino-benzonorbornene (Comp. No. Z3.11)

95 g (0.42 mol) of 9-isopropylidene-5-nitro-benzonorbornadiene (Z1.11) in 1 liter of tetrahydrofuran are exhaustively hydrogenated at 25° C. under normal pressure in the presence of 50 g of 5% Rh/C. After 3½ days, the absorption of hydrogen comes to an end. The reaction mixture is filtered, the solvent is removed in vacuo, and purification by chromatography is carried out on silica gel using ethyl acetate/hexane (1:4) as eluant. 71.8 g (85% of theory) of 9-isopropyl-5-amino-benzonorbornene are obtained in the form of an oil with a syn/anti ratio of 92:8 according to $^1$H-NMR.

The compounds of formula IV

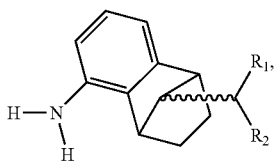

(IV)

wherein $R_1$ and $R_2$ are as defined for formula I, and wherein the ratio of compounds of formula IVa (syn)

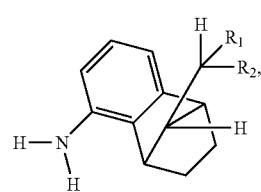

(IVa, syn)

wherein $R_1$ and $R_2$ are as defined for formula I, to compounds of formula IVb (anti)

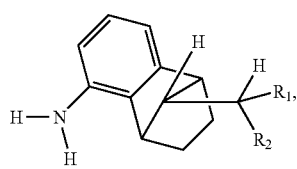

(IVb, anti)

wherein $R_1$ and $R_2$ are as defined for formula I, is from 90:10 to 99:1, are valuable intermediates in the preparation of compounds of formula I and have been developed specifically for the present process according to the invention. The present invention accordingly relates also thereto.

There are especially valuable in the preparation of compounds of formula I especially those compounds of formula IV wherein the ratio of compounds of formula IVa (syn) to compounds of formula IVb (anti) is from 91:9 to 99:1.

There are very especially valuable in the preparation of compounds of formula I especially those compounds of formula IV wherein the ratio of compounds of formula IVa (syn) to compounds of formula IVb (anti) is from 92:8 to 98:2.

There are very especially valuable in the preparation of compounds of formula I especially those compounds of formula IV wherein the ratio of compounds of formula IVa (syn) to compounds of formula IVb (anti) is approximately 95:5.

Especially suitable as intermediates in the preparation of compounds of formula I are compounds of formula IV wherein $R_1$ and $R_2$ are methyl.

As described in Scheme 2,6-nitro-anthranilic acid (compound of formula A in Scheme 2) may be used in the preparation of compounds of formula II. It has been found that 6-nitro-anthranilic acid can be prepared simply and in a high regioselective yield in accordance with the following scheme (Scheme 3):

Scheme 3:

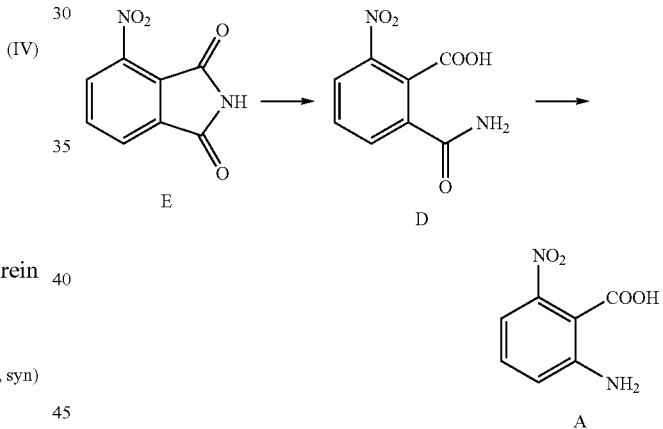

In that scheme, 3-nitro-phthalimide (compound of formula E) is converted by reaction with an aqueous base, such as, for example, aqueous sodium hydroxide, and by subsequent reaction with an aqueous acid, such as, for example, aqueous hydrochloric acid, into 6-nitrophthalamic acid (compound of formula D). 6-Nitrophthalamic acid is obtained in a high regioselective yield; typically, more than 70% measured relative to the starting material 3-nitro-phthalimide is achieved.

In a second step, 6-nitrophthalamic acid is then converted to the desired 6-nitro-anthranilic acid (compound of formula A). In that step, 6-nitrophthalamic acid may, for example, be reacted first with aqueous base, such as, for example, aqueous sodium hydroxide, and sodium hypochlorite, and then with aqueous acid, such as, for example, aqueous hydrochloric acid.

3-Nitro-phthalimide is commercially available.

Scheme 2 is explained in greater detail by way of the following Example:

EXAMPLE A3

Preparation of 6-nitro-anthranilic acid a) Preparation of 6-nitrophthalamic acid A suspension of 57.6 g of 3-nitro-phthalimide (0.3 mol) in 672 g of water is cooled to 5° C. 80 g of 30% sodium hydroxide solution (0.6 mol, 2 equivalents) are added in the shortest possible time. After 2 hours at 5° C., the reaction mixture is added at 5° C. to 65 g of 32% hydrochloric acid solution (0.57 mol, 1.9 equivalents), which is diluted beforehand with 72 ml of water. The pH value is adjusted to 2-2.5 and the crude product which crystallises out is filtered off and washed twice with water. 6-Nitrophthalamic acid is obtained in a yield of 73%.

b) Preparation of 6-nitro-anthranilic acid

A suspension of 126.3 g of 6-nitrophthalamic acid (0.6 mol) in 429 g of water is cooled to 5° C. 80 g of 30% sodium hydroxide solution (0.6 mol, 1 equivalent) are added in the course of 0.5 hour at 5° C.

The reaction mixture together with 288 g of 15.2% sodium hypochlorite solution (0.6 mol, 1 equivalent) is slowly added to a sodium hydroxide solution (235.2 g of 30% sodium hydroxide solution (1.76 mol, 3 equivalents), diluted with 280 g of water) preheated to 43° C. The temperature is maintained at 40-45° C. during the addition. After 1 hour at 40-45° C., the reaction mixture is added to a mixture of 268 g of 32% hydrochloric acid (2.35 mol, 3.9 equivalents) and 200 g of water. The temperature is maintained at 20-45° C. during the addition. The crude product which crystallises out is filtered off and washed three times with water. 6-Nitro-anthranilic acid is obtained in a yield of 70%.

The present invention relates furthermore to a process for the preparation of compounds of formula IV

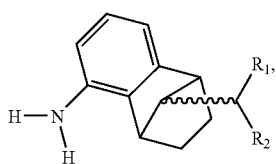
(IV)

wherein $R_1$ and $R_2$ are each independently of the other hydrogen or $C_1$-$C_5$alkyl, which comprises a) reacting a compound of formula II

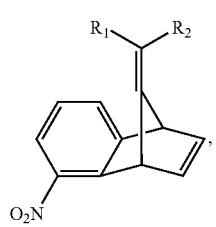
(II)

wherein $R_1$ and $R_2$ are as defined for formula IV, with at least one reducing agent to form a compound of formula III

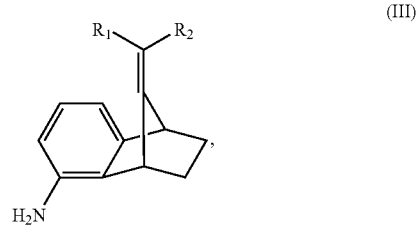
(III)

wherein $R_1$ and $R_2$ are as defined for formula IV; and
(b) converting that compound with at least one reducing agent into the compound of formula IV.

In that process according to the invention for the preparation of compounds of formula IV, sub-step (a) (preparation of compounds of formula II) and sub-step (b) (preparation of compounds of formula IV) are carried out as described above.

Also in that process according to the invention for the preparation of compounds of formula IV, by selecting suitable reaction conditions for Reaction Step a), the compound of formula III obtained in Reaction Step a) can be reacted, for example in the manner described above, to form a compound of formula IV directly, without isolation of intermediates, by complete hydrogenation.

The present invention relates furthermore to a process for the preparation of compounds of formula I

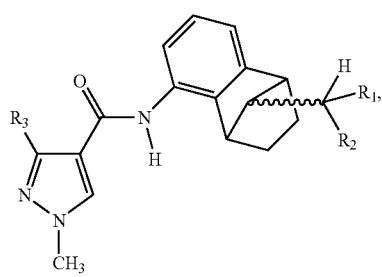
(I)

wherein $R_1$ and $R_2$ are each independently of the other hydrogen or $C_1$-$C_5$alkyl and $R_3$ is $CF_3$ or $CF_2H$, which comprises aa) reacting 6-nitro-anthranilic acid with a nitrite, selected from isoamyl nitrite and tert-butyl nitrite, and with a compound of formula C

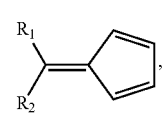
(C)

wherein $R_1$ and $R_2$ are as defined for formula I, to form a compound of formula II

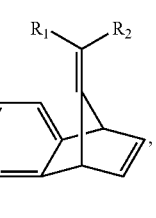
(II)

wherein $R_1$ and $R_2$ are as defined for formula I, and a) reacting that compound with a reducing agent to form a compound of formula III

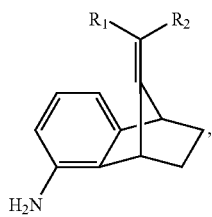

wherein $R_1$ and $R_2$ are as defined for formula I; and (b) reacting that compound with a reducing agent to form a compound of formula IV

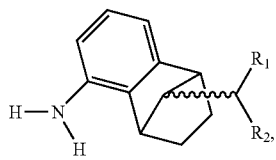

wherein $R_1$ and $R_2$ are as defined for formula I; and (c) converting that compound into the compound of formula I by reaction with a compound of formula V

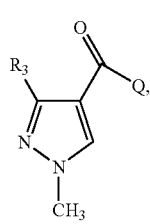

wherein Q is chlorine, bromine, iodine or hydroxy and $R_3$ is as defined for formula I.

In that process for the preparation of compounds of formula I, the Reaction Steps (a), (b) and (c) are carried out in the manner described above. Suitable aprotic solvents for Reaction Step (aa) are, for example, diethyl ether, butyl methyl ether, ethyl acetate, dichloromethane, acetone, tetrahydrofuran, toluene, 2-butanone or dimethoxyethane. Suitable reaction temperatures for Reaction Step (aa) are from ambient temperature to 100° C., preferably from 35 to 80° C.

An especially preferred embodiment of that process is a process for the preparation of compounds of formula I wherein $R_1$ and $R_2$ are methyl and $R_3$ is $CF_2H$ which comprises (aa) reacting 6-nitro-anthranilic acid with tert-butyl nitrite and with a compound of formula C wherein $R_1$ and $R_2$ are methyl to form a compound of formula II wherein $R_1$ and $R_2$ are methyl; and a) reacting that compound with hydrogen in the presence of a rhodium/carbon catalyst to form a compound of formula III wherein $R_1$ and $R_2$ are methyl; and (b) reacting that compound with hydrogen in the presence of a Raney nickel catalyst to form a compound of formula IV wherein $R_1$ and $R_2$ are methyl; and (c) converting that compound into the compound of formula I by reaction with a compound of formula V wherein 0 is hydroxy and $R_3$ is $CF_2H$, in the presence of an activating agent, preferably in the presence of bis(2-oxo-3-oxazolidinyl)-phosphinic acid chloride, the reaction being carried out in the presence of a base, preferably in the presence of triethylamine.

A more especially preferred embodiment of that process is a process for the preparation of compounds of formula I wherein $R_1$ and $R_2$ are methyl and $R_3$ is $CF_2H$ which comprises (aa) reacting 6-nitro-anthranilic acid with tert-butyl nitrite and with a compound of formula C wherein $R_1$ and $R_2$ are methyl to form a compound of formula II wherein $R_1$ and $R_2$ are methyl, dimethoxyethane being used as solvent, and a) reacting that compound with hydrogen in the presence of a rhodium/carbon catalyst to form a compound of formula III wherein $R_1$ and $R_2$ are methyl, tetrahydrofuran being used as solvent; and (b) reacting that compound with hydrogen in the presence of a Raney nickel catalyst to form a compound of formula IV wherein $R_1$ and $R_2$ are methyl, tetrahydrofuran being used as solvent; and (c) converting that compound into the compound of formula I by reaction with a compound of formula V wherein Q is hydroxy and $R_3$ is $CF_2H$, in the presence of bis(2-oxo-3-oxazolidinyl)-phosphinic acid chloride, dichloromethane being used as solvent and the reaction being carried out in the presence of triethylamine.

The compounds of formula II

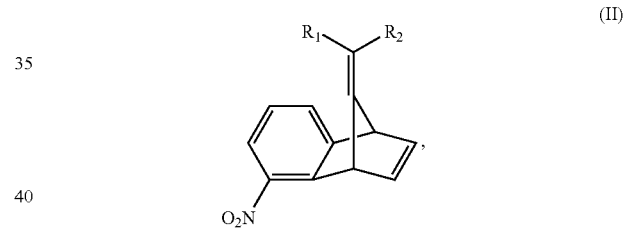

wherein $R_1$ and $R_2$ are each independently of the other hydrogen or $C_1$-$C_5$alkyl, are new and have been developed specifically for carrying out the process according to the invention. The present invention accordingly relates also to compounds of formula II wherein $R_1$ and $R_2$ are each independently of the other hydrogen or $C_1$-$C_5$alkyl. Special preference is given to compounds of formula II wherein $R_1$ and $R_2$ are methyl.

Some of the compounds of formula III

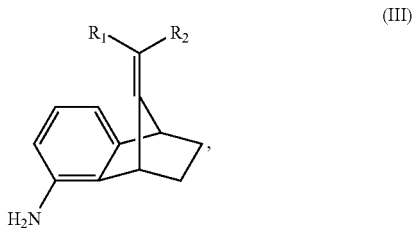

wherein $R_1$ and $R_2$ are each independently of the other hydrogen or $C_1$-$C_5$alkyl, are new and have been developed specifically for carrying out the process according to the invention. The present invention accordingly relates also to compounds of formula II wherein $R_1$ and $R_2$ are each independently of the other hydrogen or $C_1$-$C_5$alkyl, with the exception of 9-isopropyl-idene-5-amino-benzonorbornene.

Some of the compounds of formula IV

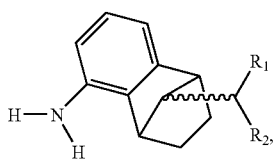
(IV)

wherein $R_1$ and $R_2$ are each independently of the other hydrogen or $C_1$-$C_5$alkyl, are new and have been developed specifically for carrying out the process according to the invention. The present invention accordingly relates also to compounds of formula IV wherein $R_1$ and $R_2$ are each independently of the other hydrogen or $C_1$-$C_5$alkyl, with the exception of 9-isopropyl-5-amino-benzonorbornene.

The compounds of formula IIA

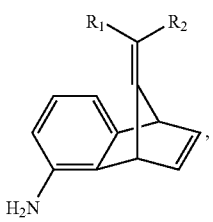
(IIA)

wherein $R_1$ and $R_2$ are each independently of the other hydrogen or $C_1$-$C_5$alkyl, are new and have been developed specifically for carrying out the process according to the invention. The present invention accordingly relates also to compounds of formula IIA wherein $R_1$ and $R_2$ are each independently of the other hydrogen or $C_1$-$C_5$alkyl. Special preference is given to compounds of formula IIA wherein $R_1$ and $R_2$ are methyl.

Further, compounds of formula I

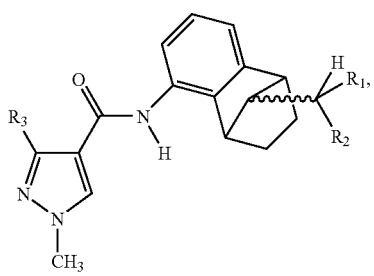
(I)

wherein $R_1$ and $R_2$ are each independently of the other hydrogen or $C_1$-$C_5$alkyl and $R_3$ is $CF_3$ or $CF_2H$, may also be prepared using compounds of formula VI

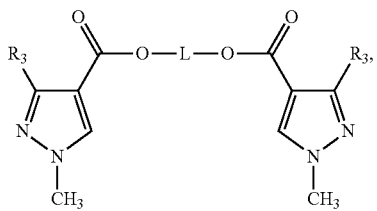
(VI)

wherein L is a $C_1$-$C_6$alkylene chain and $R_3$ is as defined for formula I, by d) reacting a compound of formula Va

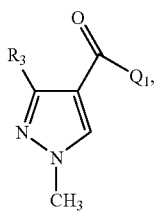
(Va)

wherein $Q_1$ is chlorine, fluorine, bromine, iodine or $C_1$-$C_6$alkoxy and $R_3$ is as defined for formula I, with a compound of formula VII

HO-L-OH (VII), wherein L is as defined for formula VI, to form a compound of formula VI; and e) converting that compound into the compound of formula I by reaction with a compound of formula IV

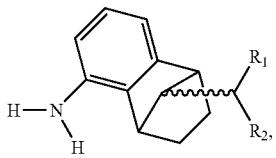
(IV)

wherein $R_1$ and $R_2$ are as defined for formula I. In that process, compounds of formula IV may be prepared in the manner described above. The present invention relates also to that preparation of compounds of formula I using compounds of formula VI and carrying out Process Steps (d) and (e).

The alkylene chains in the definitions of the substituents of the compounds of formula VI may be straight or branched and are, for example, a methylene chain or an ethylene chain, or straight or branched $C_3$-$C_6$alkylene chains, such as —$CH_2$—$CH_2$—$CH_2$— as a straight $C_3$alkylene chain or —$CH_2$—$C(CH_3)_2$—$CH_2$— as a branched $C_5$alkylene chain.

Process Step d):

Especially suitable for use in Process Step d) are compounds of formula Va wherein $Q_1$ is chlorine, fluorine, bromine or iodine and $R_3$ is as defined for formula I. Very especially preferred are compounds of formula Va wherein $Q_1$ is chlorine and $R_3$ is as defined for formula I.

Especially suitable for use in Process Step d) are compounds of formula VII wherein L is an ethylene chain.

In the reactions according to the invention, compounds of formula Va are used, for example, in equimolar amounts or in excess in relation to compounds of formula VII, preferably in an up to 4-fold excess, especially preferably in a 2-fold to 4-fold excess, very especially preferably in a 2-fold excess.

The reaction is preferably carried out in the presence of an inert solvent. Suitable solvents are, for example, chlorobenzene, dichloromethane, chloroform, toluene, tetrahydrofuran, diethyl ether, butyl methyl ether or water, and mixtures thereof, with special preference being given to chlorobenzene.

The reaction is preferably carried out in the presence of a base.

Suitable bases are, for example, amine bases, such as, for example, triethylamine or pyridine; or inorganic bases, such as carbonates, e.g. $K_2CO_3$ or $Na_2CO_3$, or hydroxides, e.g. NaOH or KOH, with preference being given to trialkylamines and special preference to triethylamine.

Suitable amounts of base for the reaction are, for example, from 1 up to 1.5 equivalents, especially from 1 up to 1.2 equivalents.

The temperatures are generally from 0° C. to 150° C., with preference being given to a range from 50° C. to 100° C. and special preference to a range from 60° C. to 100° C.

The reaction may be carried out at atmospheric pressure or at elevated pressure, with preference being given to atmospheric pressure.

The reaction time for that reaction is generally from 1 to 48 hours, preferably from 1 to 24 hours.

Compounds of formula VII are commercially available or can be prepared according to known processes.

Process Step e):

In the reactions according to the invention, compounds of formula IV are used, for example, in equimolar amounts or in excess in relation to compounds of formula VI, preferably in an up to 4-fold excess, especially preferably in a 2-fold to 4-fold excess, very especially preferably in a 2-fold excess.

The reaction may be carried out in the presence of an inert solvent. Suitable solvents are, for example, chlorobenzene, dichloromethane, chloroform, toluene, xylene, tetrahydrofuran, diethyl ether or butyl methyl ether, and mixtures thereof, with special preference being given to chlorobenzene.

The reaction may also be carried out in the absence of a solvent.

The reaction is preferably carried out in the presence of a base.

Suitable bases are, for example, amine bases, such as, for example, triethylamine or pyridine; inorganic bases, such as carbonates, e.g. $K_2CO_3$ or $Na_2CO_3$, or hydroxides, e.g. NaOH or KOH; or alkoxides, such as, for example, potassium tert-butoxide, with preference being given, for example, to potassium tert-butoxide.

Suitable amounts of base for the reaction are, for example, from 1 up to 1.5 equivalents, especially from 1 up to 1.2 equivalents.

The temperatures are generally from 0° C. to 150° C., with preference being given to a range from 50° C. to 150° C. and special preference to a range from 80° C. to 120° C.

The reaction may be carried out at atmospheric pressure or at elevated pressure, with preference being given to atmospheric pressure.

The reaction time for that reaction is generally from 1 to 48 hours, preferably from 1 to 24 hours.

The above-described process, to which the present invention also relates, is explained with reference to the following Examples:

EXAMPLE P12

Preparation of 3-difluoromethyl-1-methyl-1H-pyrazole-4-carboxylic acid 2-(3-difluoromethyl-1-methyl-1H-pyrazole-4-carbonyloxy)-ethyl ester
(Comp. No. Z4.02)

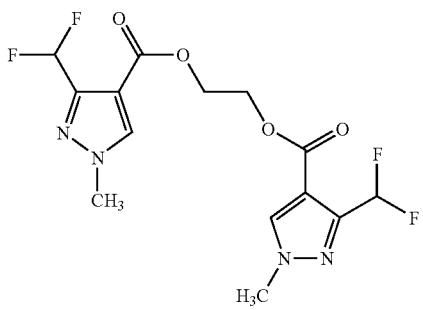

6.2 g of ethylene glycol (0.1 mol, 0.5 equivalent), 22.2 g of triethylamine (0.22 mmol, 1.1 equivalents) and 50 ml of chlorobenzene are added at ambient temperature to a 49% solution of 38.9 g of 3-difluoromethyl-1-methyl-1H-pyrazole-4-carbonyl chloride (0.2 mol) in chlorobenzene. The reaction mixture is stirred for 5 hours at 80° C. Water is added and the organic phase is extracted with methyl isobutyl ketone. 7 g of active carbon are added and the reaction mixture is filtered. The organic phase is concentrated. 35.9 g of 3-difluoromethyl-1-methyl-1H-pyrazole-4-carboxylic acid 2-(3-difluoromethyl-1-methyl-1H-pyrazole-4-carbonyloxy)-ethyl ester (yield: 95%) are obtained. $^1$H-NMR (CDCl$_3$), ppm: 7.91 (s, 2H), 7.06 (t, 2H), 4.55 (s, 4H), 3.96 (s, 6H).

EXAMPLE P13

Preparation of 3-difluoromethyl-1-methyl-1H-pyrazole-4-carboxylic acid (9-isopropyl-1,2,3,4-tetrahydro-1,4-methano-naphthalen-5-yl)-amide
(Comp. No. A.11)

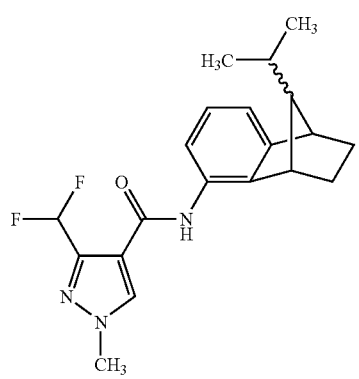

6.9 g of 9-isopropyl-5-amino-benzonorbornene (Comp. No. Z3.11, syn/anti ratio 90:10; 32.8 mmol, 2.05 equivalents) and 1.9 g of potassium tert-butoxide (16 mmol, 1 equivalent) are added to a solution of 6 g (16 mmol) of 3-difluoromethyl-1-methyl-1H-pyrazole-4-carboxylic acid 2-(3-difluoromethyl-1-methyl-1H-pyrazole-4-carbonyloxy)-ethyl ester (Comp. No. Z4.02, prepared according to Example P12) in 60 ml of chlorobenzene. The reaction mixture is heated to 95° C. and the solvent chlorobenzene is completely removed in vacuo. The reaction mixture is heated to 120° C. and stirred for 20 hours. 30 ml of chlorobenzene are then added. The organic phase is extracted twice with water, first at low pH, then at high pH. The organic phase is concentrated by distilling off chlorobenzene. 8 g of 3-difluoromethyl-1-methyl-1H-pyrazole-4-carboxylic acid (9-isopropyl-1,2,3,4-tetrahydro-1,4-methano-naphthalen-5-yl)-amide are obtained in the form of a brown oil (crude yield: 51%).

Preferred compounds of formula VI are listed in the following Table.

TABLE 6

Compounds of formula VI

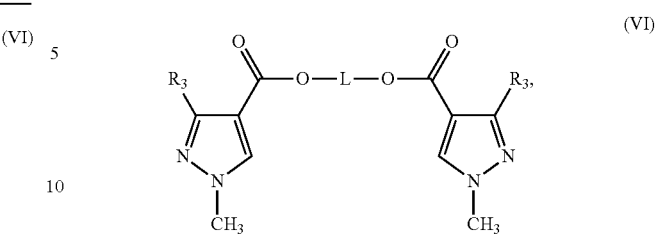

| Comp. No. | R₃ | L |
|---|---|---|
| Z4.01 | CF₂H | —CH₂— |
| Z4.02 | CF₂H | —CH₂—CH₂— |
| Z4.03 | CF₂H | —CH₂—CH₂—CH₂— |
| Z4.04 | CF₂H | —CH₂—CH₂—CH₂—CH₂— |
| Z4.05 | CF₃ | —CH₂— |
| Z4.06 | CF₃ | —CH₂—CH₂— |
| Z4.07 | CF₃ | —CH₂—CH₂—CH₂— |
| Z4.08 | CF₃ | —CH₂—CH₂—CH₂—CH₂— |

The compounds of formula VI are distinguished by ease of availability and good handling properties and are moreover reasonably priced.

The compounds of formula VI wherein L is a $C_1$-$C_6$alkylene chain and $R_3$ is $CF_3$ or $CF_2H$, are new and have been developed specifically for carrying out the process according to the invention. The present invention accordingly relates also to compounds of formula VI wherein L is a $C_1$-$C_6$alkylene chain and $R_3$ is $CF_3$ or $CF_2H$. Preference is given to compounds of formula VI wherein L is an ethylene chain. Preference is given to compounds of formula VI wherein $R_3$ is $CF_2H$. Special preference is given to compounds of formula VI wherein L is an ethylene chain and $R_3$ is $CF_2H$.

For a better overview, the above-mentioned reactions are summarised in Scheme 4.

Scheme 4:

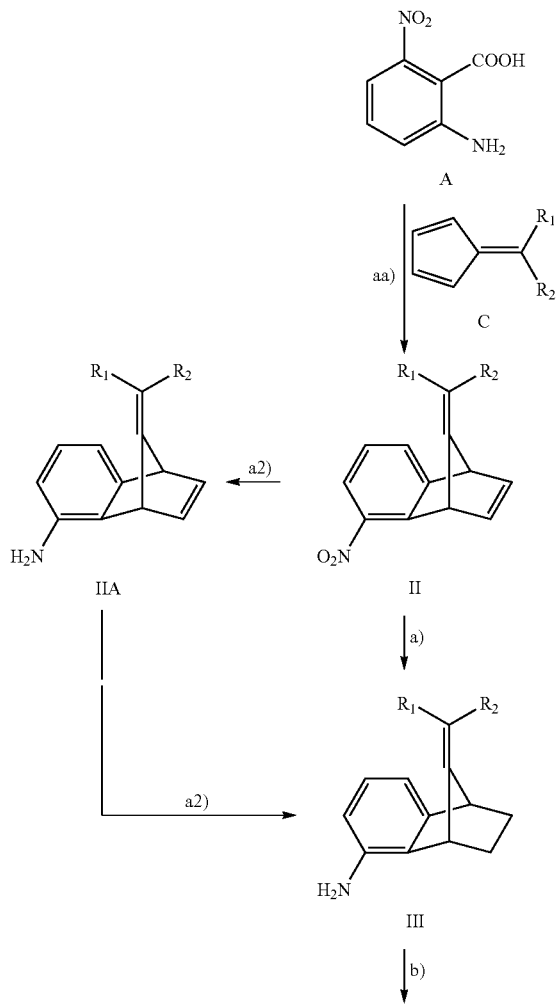

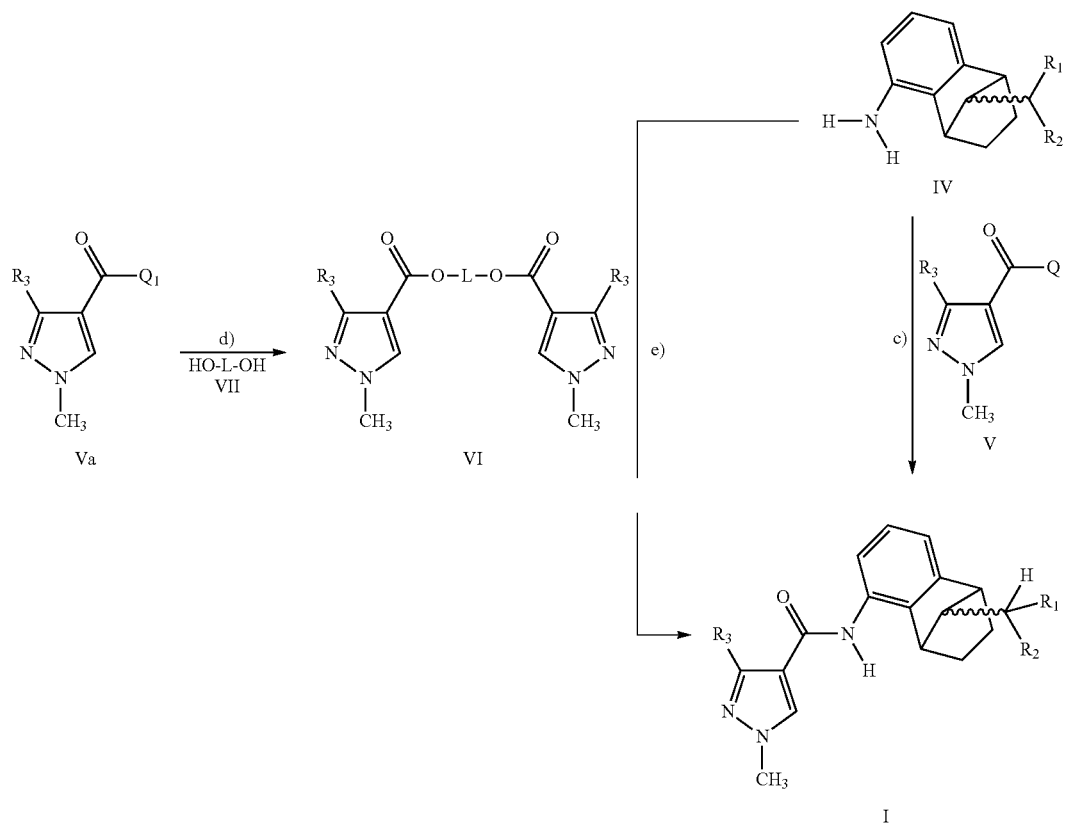

As stated above, the invention relates in various aspects inter alia to:
(1) the preparation of compounds of formula I starting from compounds of formula II using Steps a), b) and c);
(2) the preparation of compounds of formula I starting from compounds of formula II using Steps a2), b) and c);
(3) the preparation of compounds of formula IV starting from compounds of formula II using Steps a) and b);
(4) the preparation of compounds of formula IV starting from compounds of formula II using Steps a2) and b);
(5) the preparation of compounds of formula I starting from compounds of formula A using Steps aa), a), b) and c);
(6) the preparation of compounds of formula I starting from compounds of formula A using Steps aa), a2), b) and c);
(7) the preparation of compounds of formula I starting from compounds of formula II using Steps a), b), d) and e); and
(8) the preparation of compounds of formula I starting from compounds of formula II using Steps a2), b), d) and e).

The invention relates also to intermediates for use in the above processes.

The present invention further relates to a novel crystal modification of syn-3-difluoromethyl-1-methyl-1H-pyrazole-4-carboxylic acid (9-isopropyl-1,2,3,4-tetrahydro-1,4-methano-naphthalen-5-yl)-amide, compositions comprising it and to the use thereof in the control of fungus infestation in cultivated plants.

3-difluoromethyl-1-methyl-1H-pyrazole-4-carboxylic acid (9-isopropyl-1,2,3,4-tetrahydro-1,4-methano-naphthalen-5-yl)-amide (Comp. No. A.11) is effective against a number of diseases caused by phytopathogenic fungi. This amide is a chiral molecule which can occur in 4 stereoisomeric forms, shown as enantiomers of formulae A.11 (syn1), A.11 (syn2), A.11 (anti1) and A.11 (anti2):

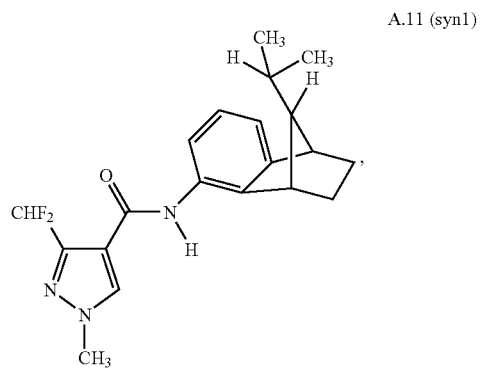

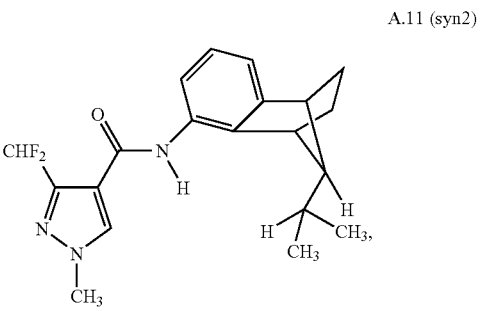

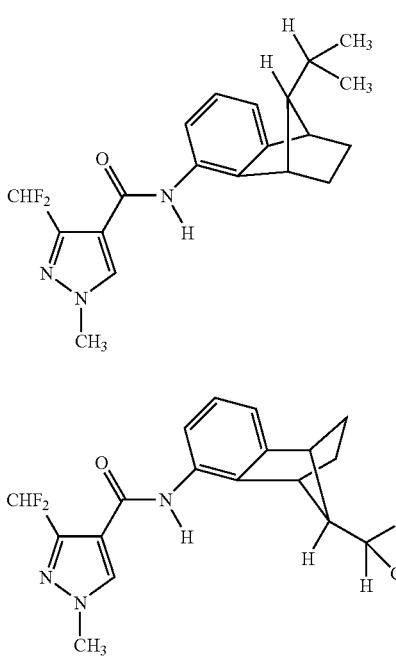

According to the invention "syn-3-difluoromethyl-1-methyl-1H-pyrazole-4-carboxylic acid (9-isopropyl-1,2,3,4-tetrahydro-1,4-methano-naphthalen-5-yl)-amide" means a racemic mixture of compounds of formula A.11 (syn1) and compounds of formula A.11 (syn2).

Crystalline material of syn-3-difluoromethyl-1-methyl-1H-pyrazole-4-carboxylic acid (9-isopropyl-1,2,3,4-tetrahydro-1,4-methano-naphthalen-5-yl)-amide having a single melting point of 110-112° C. (diastereomeric purity: 90%) is disclosed in WO 04/035589. This crystalline material is defined herein as "crystal modification A" of syn-3-difluoromethyl-1-methyl-1H-pyrazole-4-carboxylic acid (9-isopropyl-1,2,3,4-tetrahydro-1,4-methano-naphthalen-5-yl)-amide.

Various crystal modifications of chemical compounds can exhibit very different physical properties, which may lead to unforseeable problems during technical preparation and processing of these compounds. The characteristics of crystal modifications frequently have a crucial influence on the separating ability (filtration), stirrability (crystal volume), surface activity (foaming), rate of drying, solubility, quality, formulating ability and storage stability and bioefficacy of for example pharmaceutically and agronomically active compounds. For example, the grinding and formulating properties (e.g. granulating) of products may be completely different, depending on the respective crystal modification. Since, depending on the envisaged formulating process, different physical properties of the respective products are of importance, it is especially advantageous to find the optimally suited crystal form for the respective formulating process.

Furthermore, a modification can suddenly transform into another undesired modification under certain thermodynamic conditions. The number of polymorphic states are unpredictable. The most stable polymeric state may not form because the rate of formation of new crystals from a solution may be extremely slow.

It is therefore the aim of the present invention to specifically provide novel crystal modifications of syn-3-difluoromethyl-1-methyl-1H-pyrazole-4-carboxylic acid (9-isopropyl-1,2,3,4-tetrahydro-1,4-methano-naphthalen-5-yl)-amide with good properties in relation to the formulation of the active ingredient and its storability.

The present invention relates to crystal modification B of syn-3-difluoromethyl-1-methyl-1H-pyrazole-4-carboxylic acid (9-isopropyl-1,2,3,4-tetrahydro-1,4-methano-naphthalen-5-yl)-amide, wherein said crystal modification is characterized by an x-ray powder diffraction pattern, expressed in terms of d-spacings and relative intensities, wherein said an x-ray powder diffraction pattern comprises the following characteristic lines: 13.42 Å (strong), 9.76 Å (medium), 6.93 Å (medium), 6.74 Å (medium), 4.79 Å (medium), 4.73 Å (medium), and 3.66 Å (medium). The x-ray powder diffraction pattern has been obtained by using a Bruker-AXS D8 Advanced Powder X-ray diffractometer, source: Cu Kα1.

Crystal modification B differs from crystal modification A with respect to thermodynamic stability, physical parameters, such as the absorption pattern of IR and Raman spectra, in x-ray structure investigations and in their solubility in water or other commonly used liquid carriers in agrochemical formulations.

The modification B has significant advantages compared with the modification A. Thus, for example, DSC, solubility tests and other experiments, have shown that the modification B surprisingly has substantially better thermodynamic stability than the modification A.

For example, the water solubility of modification B is lower than the water solubility of modification A over relevant temperature ranges. In aqueous dispersions the polymorph with the lowest solubility is most stable. A polymorph with a higher solubility is unstable, because the surrounding water phase will be supersaturated relative to the more stable polymorph leading to solution of the more unstable polymorph and crystallisation of the more stable polymorph. The resulting change of particle sizes could lead to a change of the stability of the formulated dispersion.

It is particularly important for a fungicide that its agrochemical formulation ensures high and reproducible stability over a long period. These preconditions are fulfilled by incorporation of the compound syn-3-difluoromethyl-1-methyl-1H-pyrazole-4-carboxylic acid (9-isopropyl-1,2,3,4-tetrahydro-1,4-methano-naphthalen-5-yl)-amide of the crystal modification B, owing to its high thermodynamic stability compared with crystal modification A. In particular, this is displayed in a solid agrochemical dosage form. If an active ingredient is subjected to a conversion process, this may readily also affect the stability of the solid formulation.

Accordingly, agrochemical active ingredients or polymorphic forms thereof which are of primary interest for development of new active ingredients are those which exhibit high stability and do not have the above-mentioned disadvantages. The crystal modification B fulfills these preconditions.

Crystal modification B was prepared as described in examples P5, P6 and P14. Crystal modification A was prepared as described in example A4. Crystal modification B can also be prepared by seeded crystallisation from methanol/water mixtures; typically, a 10% seed loading can be used. For example, crystal modification B can also be prepared by seeded crystallisation from 20% water/methanol.

Modification B has an X-ray powder pattern with characteristic lines with interplanar spacings (d values in Angstrom) of 13.42 Å (strong), 9.76 Å (medium), 6.93 Å (medium), 6.74 Å (medium), 4.79 Å (medium), 4.73 Å (medium), and 3.66 Å (medium) (see table 7 or FIG. 1). In contrast, modification A has an X-ray powder pattern with characteristic lines with interplanar spacings (d values) of 21.98 Å (medium), 10.81 Å

(weak), 8.79 Å (weak), 6.51 Å (weak), 4.65 Å (medium) and 4.20 Å (medium) (see table 8 or FIG. 2). The x-ray powder diffraction patterns have been obtained by using a Bruker-AXS D8 Advanced Powder X-ray diffractometer, source: Cu Kα1.

TABLE 7

Characterization of the modification B (X-ray powder pattern)

| 2-Theta | d-Spacing (Å) | Strength |
| --- | --- | --- |
| 6.59 | 13.42 | strong |
| 9.08 | 9.76 | medium |
| 12.85 | 6.93 | medium |
| 13.22 | 6.74 | medium |
| 14.21 | 6.23 | weak |
| 15.65 | 5.66 | medium |
| 18.32 | 4.84 | medium |
| 18.77 | 4.79 | medium |
| 19.02 | 4.73 | medium |
| 22.31 | 3.98 | medium |
| 23.35 | 3.81 | medium |
| 24.88 | 3.66 | medium |

TABLE 8

Characterization of the modification A (X-ray powder pattern)

| 2-Theta | d-Spacing (Å) | Strength |
| --- | --- | --- |
| 4.02 | 21.98 | medium |
| 6.48 | 13.64 | weak |
| 8.19 | 10.81 | weak |
| 9.06 | 9.76 | weak |
| 10.09 | 8.79 | medium |
| 11.63 | 7.60 | medium |
| 12.74 | 9.94 | weak |
| 13.68 | 6.51 | weak |
| 14.40 | 6.15 | weak |
| 18.63 | 4.76 | weak |
| 19.35 | 4.65 | medium |
| 20.96 | 4.23 | medium |

In the Raman Spectrum modification B differs from modification A in the shape and in the relative intensity of many bands (see FIGS. 3 and 4). For example, the apparatus Thermo Electron Almega Raman Microscope (785 nm, High Resolution settings) can be used for the recording of each of the Raman Spectra.

Characteristic for modification B is also the thermogram in DSC (differential scanning calorimetry, see FIG. 5). It has an endothermic peak in the range from 120° C. to 128° C. depending on purity. For example, crystal modification B in pure form has a peak temperature of 128° C. and an endothermic signal around 90 J/g. This thermogram is characteristically different from the thermogram of the modification A (see FIG. 6), which has an endothermic peak at about 112° C. and an endothermic signal of 76 J/g. The measurement was carried out on a Metler Toledo 820 DSC in a closed pan with a heating rate of 10 K/minute. The typical sample quantity is about 5 mg.

The present invention preferably relates to crystal modification B of syn-3-difluoromethyl-1-methyl-1H-pyrazole-4-carboxylic acid (9-isopropyl-1,2,3,4-tetrahydro-1,4-methano-naphthalen-5-yl)-amide, wherein said crystal modification is characterized by an x-ray powder diffraction pattern, expressed in terms of d-spacings and relative intensities, wherein said an x-ray powder diffraction pattern comprises the following characteristic lines: 13.42 Å (strong), 9.76 Å (medium), 6.93 Å (medium), 6.74 Å (medium), 6.23 Å (weak), 5.66 Å (medium), 4.84 Å (medium), 4.79 Å (medium), 4.73 Å (medium), 3.98 Å (medium), 3.81 Å (medium) and 3.66 Å (medium).

The present invention preferably relates to crystal modification B of syn-3-difluoromethyl-1-methyl-1H-pyrazole-4-carboxylic acid (9-isopropyl-1,2,3,4-tetrahydro-1,4-methano-naphthalen-5-yl)-amide, wherein said crystal modification is characterized having the x-ray powder diffraction pattern depicted in FIG. 1.

The present invention preferably relates to crystal modification B of syn-3-difluoromethyl-1-methyl-1H-pyrazole-4-carboxylic acid (9-isopropyl-1,2,3,4-tetrahydro-1,4-methano-naphthalen-5-yl)-amide, wherein said crystal modification is characterized by having in the thermogram in differential scanning calorimetry an endothermic signal with a peak in the range from 120° C. to 128° C.

The present invention preferably relates to crystal modification B of syn-3-difluoromethyl-1-methyl-1H-pyrazole-4-carboxylic acid (9-isopropyl-1,2,3,4-tetrahydro-1,4-methano-naphthalen-5-yl)-amide in substantially pure form. According to the invention "substantially pure" means preferably at least 75% by weight of crystal modification B of syn-3-difluoromethyl-1-methyl-1H-pyrazole-4-carboxylic acid (9-isopropyl-1,2,3,4-tetrahydro-1,4-methano-naphthalen-5-yl)-amide), more preferably at least 80% by weight.

The present invention preferably relates to crystal modification B of syn-3-difluoromethyl-1-methyl-1H-pyrazole-4-carboxylic acid (9-isopropyl-1,2,3,4-tetrahydro-1,4-methano-naphthalen-5-yl)-amide in pure form. According to the invention "pure" means at least 90% by weight of crystal modification B of syn-3-difluoromethyl-1-methyl-1H-pyrazole-4-carboxylic acid (9-isopropyl-1,2,3,4-tetrahydro-1,4-methano-naphthalen-5-yl)-amide, more preferably at least 95% by weight, even more preferably at least 98% by weight.

The present invention preferably relates to crystal modification B of syn-3-difluoromethyl-1-methyl-1H-pyrazole-4-carboxylic acid (9-isopropyl-1,2,3,4-tetrahydro-1,4-methano-naphthalen-5-yl)-amide in highly pure form. According to the invention "highly pure" means substantially homogenous crystal modification B of syn-3-difluoromethyl-1-methyl-1H-pyrazole-4-carboxylic acid (9-isopropyl-1,2,3,4-tetrahydro-1,4-methano-naphthalen-5-yl)-amide.

The crystal modification B of syn-3-difluoromethyl-1-methyl-1H-pyrazole-4-carboxylic acid (9-isopropyl-1,2,3,4-tetrahydro-1,4-methano-naphthalen-5-yl)-amide can be used against microorganisms, that cause diseases on useful plants, in particular against phytopathogenic fungi. The crystal modification B is effective especially against phytopathogenic fungi belonging to the following classes: *Ascomycetes* (e.g. *Venturia, Podosphaera, Erysiphe, Monilinia, Mycosphaerella, Uncinula*); Basidiomycetes (e.g. the genus *Hemileia, Rhizoctonia, Phakopsora, Puccinia, Ustilago, Tilletia*); Fungi imperfecti (also known as Deuteromycetes; e.g. *Botrytis, Helminthosporium, Rhynchosporium, Fusarium, Septoria, Cercospora, Alternaria, Pyricularia* and *Pseudocercosporella*); Oomycetes (e.g. *Phytophthora, Peronospora, Pseudoperonospora, Albugo, Bremia, Pythium, Pseudosclerospora, Plasmopara*).

According to the invention "useful plants" typically comprise the following species of plants: pome fruits; stone fruits; grapes; strawberries; tomatoes; potatoes; peppers; lettuce; sugarbeets; peanuts; wheat; rye; barley; triticale; oats; rice; maize; cotton; soybeans; oilseed rape; pulse crops; sunflower; coffee; tea; sugarcane; banana; vegetables, such as cucumbers, beans and cucurbits; tobacco; fruit and ornamentals in horticulture and viticulture; turf and lawns.

The term "useful plants" is to be understood as including also (1) plants that have been rendered tolerant to herbicides like bromoxynil or classes of herbicides as a result of conventional methods of breeding or genetic engineering; (2) plants which have been so transformed by the use of recombinant DNA techniques that they are capable of synthesising one or more selectively acting toxins, such as are known, for example, from toxin-producing bacteria, especially those of the genus *Bacillus*; (3) plants which have been so transformed by the use of recombinant DNA techniques that they are capable of synthesising antipathogenic substances having a selective action, such as, for example, the so-called "pathogenesis-related proteins"; and (4) plants which may also comprise one or more "output traits" (traits which provide enhanced product quality), such as traits which alter the fatty acid composition of the plant/seed, for example provide altered levels of oleic acid and/or stearic acid or traits which provide industrial products such as, for example, pharmaceuticals (including antibodies) and also industrial enzymes (e.g. phytase, xylanase, glucanase).

The crystal modification B is also effective to protect natural substances of plant and/or animal origin, their processed forms or technical material against attack of fungi.

The amount of the crystal modification B to be applied, will depend on various factors, such as the subject of the treatment, such as, for example plants, soil or seeds; the type of treatment, such as, for example spraying, dusting or seed dressing; the purpose of the treatment, such as, for example prophylactic or therapeutic; the type of fungi to be controlled or the application time.

The crystal modification B can also be used together with further fungicides, bactericides, herbicides, insecticides, nematicides, molluscicides or mixtures of several of those active ingredients. The crystal modification B may be employed in any conventional form, for example in the form of a suspension concentrate (SC), an emulsion concentrate (EC) or a flowable concentrate for seed treatment (FS). When using the crystal modification B, it is applied to the useful plants, the locus thereof or propagation material thereof, typically as a composition (a conventional form) as described above.

The crystal modification B is applied by treating the fungi, the useful plants, the locus thereof or the propagation material thereof with the crystal modification B. Crystal modification B may be applied before or after infection of the useful plants or the propagation material thereof by the fungi. The term "locus" of a useful plant as used herein is intended to embrace the place on which the useful plants are growing, where the plant propagation materials of the useful plants are sown or where the plant propagation materials of the useful plants will be placed into the soil. An example for such a locus is a field, on which crop plants are growing. The term "plant propagation material" is understood to denote generative parts of a plant, such as seeds, which can be used for the multiplication of the latter, and vegetative material, such as cuttings or tubers, for example potatoes; preferably "plant propagation material" denotes seeds.

Crystal modification B is useful for controlling the following plant diseases on useful plants: *Alternaria* species in fruit and vegetables; *Ascochyta* species in pulse crops; *Botrytis cinerea* in strawberries, tomatoes, sunflower, pulse crops, vegetables and grapes, such as *Botrytis cinerea* on grape; *Cercospora arachidicola* in peanuts; *Cochliobolus sativus* in cereals; *Colletotrichum* species in pulse crops; *Erysiphe* species in cereals; such as *Erysiphe graminis* on wheat and *Erysiphe graminis* on barley; *Erysiphe cichoracearum* and *Sphaerotheca fuliginea* in cucurbits; *Fusarium* species in cereals and maize; *Gaumannomyces graminis* in cereals and lawns; *Helminthosporium* species in maize, rice and potatoes; *Hemileia vastatrix* on coffee; *Microdochium* species in wheat and rye; *Mycosphaerella fijiensis* in banana; *Phakopsora* species in soybeans, such as *Phakopsora pachyrizi* in soybeans; *Puccinia* species in cereals, broadleaf crops and perennial plants; such as *Puccinia recondita* on wheat, *Puccinia striiformis* on wheat and *Puccinia recondita* on barley; *Pseudocercosporelia* species in cereals, such as *Pseudocercosporella herpotrichoides* in wheat; *Phragmidium mucronatum* in roses; *Podosphaera* species in fruits; *Pyrenophora* species in barley, such as *Pyrenophora teres* on barley; *Pyricularia oryzae* in rice; *Ramularia collo-cygni* in barley; *Rhizoctonia* species in cotton, soybean, cereals, maize, potatoes, rice and lawns, such as *Rhizoctonia solani* on potato, rice, turf and cotton; *Rhynchosporium secalis* on barley, *Rhynchosporium secalis* on rye; *Sclerotinia* species in lawns, lettuce, vegetables and oil seed rape, such as *Sclerotinia sclerotiorum* on oilseed rape and *Sclerotinia homeocarpa* on turf; *Septoria* species in cereals, soybean and vegetables, such as *Septoria tritici* on wheat, *Septoria nodorum* on wheat and *Septoria* glycines on soybean; *Sphacelotheca reilliana* in maize; *Tilletia* species in cereals; *Uncinula necator, Guignardia bidwellii* and *Phomopsis viticola* in vines; *Urocystis occulta* in rye; *Uromyces* species in beans; *Ustilago* species in cereals and maize; *Venturia* species in fruits, such as *Venturia inequalis* on apple; *Monilinia* species on fruits; and/or *Penicillium* species on citrus and apples.

When applied to the useful plants, the crystal modification B is applied at a rate of 5 to 2000 g a.i./ha, particularly 10 to 1000 g a.i./ha, e.g. 50, 75, 100 or 200 g a.i./ha; when applied in the form of a composition, the application rate typically range from 20 to 4000 g of total composition per hectare. When used for treating seed, rates of 0.001 to 50 g of the crystal modification B per kg of seed, preferably from 0.01 to 10 g per kg of seed are generally sufficient.

The present invention furthermore relates to a fungicidal composition comprising as active ingredient crystal modification B of syn-3-difluoromethyl-1-methyl-1H-pyrazole-4-carboxylic acid (9-isopropyl-1,2,3,4-tetrahydro-1,4-methano-naphthalen-5-yl)-amide in a fungicidally effective amount together with a suitable carrier.

These compositions of the invention may be employed in any conventional form, for example in the form of a twin pack, a suspension concentrate (SC), a suspo-emulsion (SE), a water dispersible granule (WG), an emulsifiable granule (EG), an oil dispersion (OD), an oil miscible flowable (OF), an ultra-low volume suspension (SU), a wettable powder (WP), a technical concentrate (TK), a dispersible concentrate (DC), a powder for dry seed treatment (DS), a flowable concentrate for seed treatment (FS), a water dispersible powder for seed treatment (WS) or any technically feasible formulation in combination with agriculturally acceptable adjuvants.

Such compositions may be produced in conventional manner, e.g. by mixing the active ingredient or active ingredients with appropriate formulation inerts (diluents, solvents, fillers and optionally other formulating ingredients such as surfactants, biocides, anti-freeze, stickers, thickeners and compounds that provide adjuvancy effects). Particularly formulations to be applied in spraying forms, such as water dispersible concentrates (e.g. SC, DC, SE, and the like), wettable powders and granules, may contain surfactants such as wetting and dispersing agents and other compounds that provide adjuvancy effects, e.g. the condensation product of formaldehyde with naphthalene sulphonate, an alkylarylsulphonate, a lignin sulphonate, a fatty alkyl sulphate, and ethoxylated alkylphenol and an ethoxylated fatty alcohol.

These compositions may also comprise further pesticides, such as, for example, fungicides, insecticides or herbicides.

A seed dressing formulation is applied in a manner known per se to the seeds employing the compositions according to the invention and a diluent in suitable seed dressing formulation form, e.g. as an aqueous suspension or in a dry powder form having good adherence to the seeds. Such seed dressing formulations are known in the art.

In general, the formulations include from 0.01 to 90% by weight of the active agent, from 0 to 20% agriculturally acceptable surfactant and 10 to 99.99% solid or liquid formulation inerts and adjuvant(s), the active agent being at least the crystal modification B, and optionally comprising other active agents. Concentrated forms of compositions generally contain in between about 2 and 80%, preferably between about 5 and 70% by weight of active agent. Application forms of the compositions may for example contain from 0.01 to 20% by weight, preferably from 0.01 to 5% by weight of active agent. Whereas commercial products will preferably be formulated as concentrates, the end user will normally employ diluted formulations.

The present invention furthermore relates to a method of controlling phytopathogenic diseases on useful plants or on propagation material thereof, which comprises applying to the useful plants, the locus thereof or propagation material thereof a composition comprising as active ingredient crystal modification B of syn-3-difluoromethyl-1-methyl-1H-pyrazole-4-carboxylic acid (9-isopropyl-1,2,3,4-tetrahydro-1,4-methano-naphthalen-5-yl)-amide in a fungicidally effective amount together with a suitable carrier.

The preparation of modification B is carried out, for example, as described in the embodiments below.

EXAMPLE P14

Preparation of syn-3-difluoromethyl-1-methyl-1H-pyrazole-4-carboxylic acid (9-isopropyl-1,2,3,4-tetrahydro-1,4-methano-naphthalen-5-yl)-amide (Purity: >99%) in Modification B 240 g of crystalline 3-difluoromethyl-1-methyl-1H-pyrazole-4-carboxylic acid (9-isopropyl-1,2,3,4-tetrahydro-1,4-methano-naphthalen-5-yl)-amide (purity: 97.6%; syn/anti ratio 94:6), prepared starting from 9-isopropyl-5-amino-benzonorbornene (syn/anti ratio 90:10) as described in example P6, was mixed with 560 g methanol at a temperature of 60° C. The mixture was heated to 65° C. and stirred until the crystalline material was dissolved. The solution was cooled over a time period of 20 minutes to a temperature of 40° C. and then over a time period of 2 hours to 25° c. During that time period a precipitate was formed. The precipitate was filtered at 25° C. and dried at 60° C. under vacuum. 113 g of pure syn-3-difluoromethyl-1-methyl-1H-pyrazole-4-carboxylic acid (9-isopropyl-1,2,3,4-tetrahydro-1,4-methano-naphthalen-5-yl)-amide (purity: >99%, m.p. 128° C., yield: 47%) was obtained. The crystalline material was analyzed by differential scanning calorimetry and x-ray diffraction and was identified as crystal modification B of syn-3-difluoromethyl-1-methyl-1H-pyrazole-4-carboxylic acid (9-isopropyl-1,2,3,4-tetrahydro-1,4-methano-naphthalen-5-yl)-amide no presence of modification A was detected (see FIGS. 1, 3 and 5).

EXAMPLE A4

Preparation of syn-3-difluoromethyl-1-methyl-1H-pyrazole-4-carboxylic acid (9-isopropyl-1,2,3,4-tetrahydro-1,4-methano-naphthalen-5-yl)-amide in Modification A Crystalline syn-3-difluoromethyl-1-methyl-1H-pyrazole-4-carboxylic acid (9-isopropyl-1,2,3,4-tetrahydro-1,4-methano-naphthalen-5-yl)-amide (purity of syn/anti-compounds: 94.1%; syn/anti ratio 84:16) was prepared as described in example P6 starting from 9-isopropyl-5-amino-benzonorbornene (syn/anti ratio 87:13). The crystalline material was analyzed by differential scanning calorimetry, Raman spectroscopy and x-ray diffraction and was identified as crystal modification A of syn-3-difluoromethyl-1-methyl-1H-pyrazole-4-carboxylic acid (9-isopropyl-1,2,3,4-tetrahydro-1,4-methano-naphthalen-5-yl)-amide, no presence of modification B was detected (see FIGS. 2, 4 and 6).

FORMULATION EXAMPLES

The Examples which follow serve to illustrate the invention, "active ingredient" denoting the crystal modification B of syn-3-difluoromethyl-1-methyl-1H-pyrazole-4-carboxylic acid (9-isopropyl-1,2,3,4-tetrahydro-1,4-methano-naphthalen-5-yl)-amide.

| Suspension concentrates | |
|---|---|
| active ingredient | 40% |
| propylene glycol | 10% |
| nonylphenol polyethylene glycol ether (15 mol of ethylene oxide) | 6% |
| Sodium lignosulfonate | 10% |
| carboxymethylcellulose | 1% |
| silicone oil (in the form of a 75% emulsion in water) | 1% |
| Water | 32% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

| Wettable powders | a) | b) | c) |
|---|---|---|---|
| active ingredient | 25% | 50% | 75% |
| sodium lignosulfonate | 5% | 5% | — |
| sodium lauryl sulfate | 3% | — | 5% |
| sodium diisobutylnaphthalenesulfonate | — | 6% | 10% |
| phenol polyethylene glycol ether (7-8 mol of ethylene oxide) | — | 2% | — |
| highly dispersed silicic acid | 5% | 10% | 10% |
| Kaolin | 62% | 27% | — |

The active ingredient is thoroughly mixed with the adjuvants and the mixture is thoroughly ground in a suitable mill, affording wettable powders that can be diluted with water to give suspensions of the desired concentration.

| Powders for dry seed treatment | a) | b) | c) |
|---|---|---|---|
| active ingredient | 25% | 50% | 75% |
| light mineral oil | 5% | 5% | 5% |
| highly dispersed silicic acid | 5% | 5% | — |
| Kaolin | 65% | 40% | — |
| Talcum | — | — | 20 |

The active ingredient is thoroughly mixed with the adjuvants and the mixture is thoroughly ground in a suitable mill, affording powders that can be used directly for seed treatment.

| Dusts | a) | b) | c) |
|---|---|---|---|
| Active ingredient | 5% | 6% | 4% |
| talcum | 95% | — | — |
| Kaolin | — | 94% | — |
| mineral filler | — | — | 96% |

Ready-for-use dusts are obtained by mixing the active ingredient with the carrier and grinding the mixture in a suitable mill. Such powders can also be used for dry dressings for seed.

| Extruder granules | |
|---|---|
| Active ingredient | 15% |
| sodium lignosulfonate | 2% |
| carboxymethylcellulose | 1% |
| Kaolin | 82% |

The active ingredient is mixed and ground with the adjuvants, and the mixture is moistened with water. The mixture is extruded and then dried in a stream of air.

| Coated granules | |
|---|---|
| Active ingredient | 8% |
| polyethylene glycol (mol. wt. 200) | 3% |
| Kaolin | 89% |

The finely ground active ingredient is uniformly applied, in a mixer, to the kaolin moistened with polyethylene glycol. Non-dusty coated granules are obtained in this manner.

| Flowable concentrates for seed treatment | |
|---|---|
| active ingredient | 40% |
| propylene glycol | 5% |
| copolymer butanol PO/EO | 2% |
| tristyrenephenole with 10-20 moles EO | 2% |
| 1,2-benzisothiazolin-3-one (in the form of a 20% solution in water) | 0.5% |
| monoazo-pigment calcium salt | 5% |
| Silicone oil (in the form of a 75% emulsion in water) | 0.2% |
| Water | 45.3% |

The finely ground active ingredient is intimately mixed with the adjuvants, giving a suspension concentrate from which suspensions of any desired dilution can be obtained by dilution with water. Using such dilutions, living plants as well as plant propagation material can be treated and protected against infestation by microorganisms, by spraying, pouring or immersion.

DESCRIPTION OF FIGURES

FIG. 1 shows the x-ray pattern, FIG. 3 shows the Raman spectrum and FIG. 5 shows the DSC plot of crystal modification B as prepared in example P14.

FIG. 2 shows the x-ray pattern, FIG. 4 shows the Raman spectrum and FIG. 6 shows the DSC plot of crystal modification A as prepared in example A4.

FIG. 7 shows the x-ray pattern of crystal modification B as prepared in example P5.

FIG. 8 shows the x-ray pattern of crystal modification B as prepared in example P6.

What is claimed is:

1. A process for the preparation of a compound of formula I:

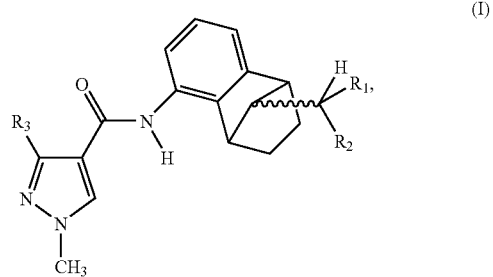

wherein $R_1$ and $R_2$ are each independently hydrogen or $C_1$-$C_5$alkyl, and $R_3$ is $CF_3$ or $CF_2H$, which comprises:

a) reacting a compound of formula II:

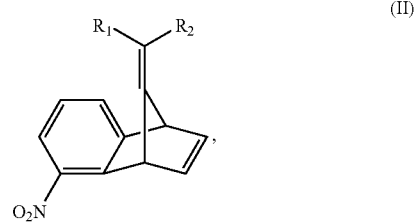

wherein $R_1$ and $R_2$ are as defined for formula I, with at least one reducing agent to form a compound of formula III:

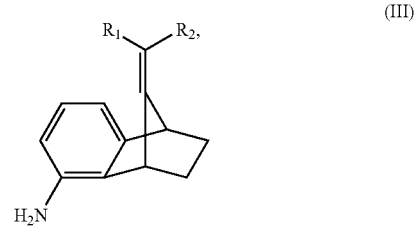

wherein $R_1$ and $R_2$ are as defined for formula I;

(b) reacting the compound of formula III with at least one reducing agent to form a compound of formula IV:

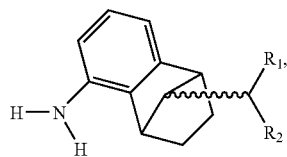

wherein $R_1$ and $R_2$ are as defined for formula I; and
(c) converting the compound of formula IV into the compound of formula I by reaction with a compound of formula V:

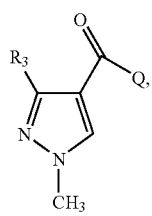

wherein Q is chlorine, fluorine, bromine, iodine, hydroxy or $C_1$-$C_6$alkoxy, and $R_3$ is as defined for formula I.

2. A process according to claim 1 wherein, in the compound of formula I, $R_1$ and $R_2$ are methyl and $R_3$ is $CF_2H$.

3. A process according to claim 1 wherein, in said converting step, the compound of formula IV is reacted with a compound of formula V wherein Q is chlorine, fluorine or bromine and $R_3$ is as defined for formula I.

4. A process according to claim 1 wherein, in said converting step, the compound of formula IV is reacted with a compound of formula V wherein Q is chlorine, bromine, iodine or hydroxy and $R_3$ is as defined for formula I.

5. A process according to claim 4 wherein a single reducing agent is used in said step of reacting the compound of formula II.

6. A process according to claim 4 wherein the compound of formula III obtained in said step of reacting the compound of formula II is reacted to form a compound of formula IV directly, without isolation of an intermediate.

7. A process according to claim 4 wherein, in said converting step, the compound of formula IV is reacted with a compound of formula V wherein Q is hydroxy and $R_3$ is as defined for formula I.

8. A process according to claim 4 wherein, in a compound of formula I, $R_1$ and $R_2$ are methyl and $R_3$ is $CF_2H$.

9. A process according to claim 4 wherein, in said step of reacting the compound of formula III, hydrogen in the presence of a rhodium catalyst is used as reducing agent and the compound of formula III:

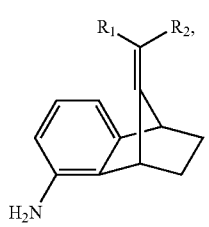

wherein $R_1$ and $R_2$ are as defined for formula I, is reacted to form a compound of formula IV:

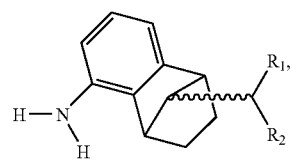

wherein $R_1$ and $R_2$ are as defined for formula I and wherein the ratio of compound of formula IVa (syn)-:

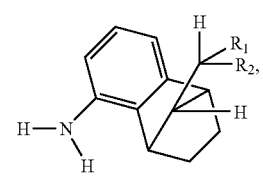

wherein $R_1$ and $R_2$ are as defined for formula I, to compound of formula IVb (anti):

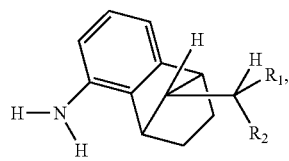

wherein $R_1$ and $R_2$ are as defined for formula I, is more than 90:10.

10. A process for the preparation of a compound of formula I:

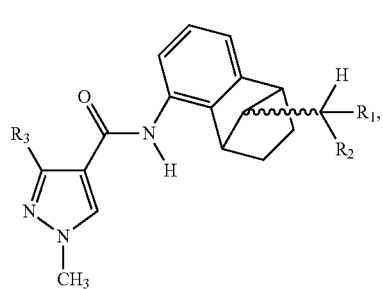

wherein $R_1$ and $R_2$ are each independently hydrogen or $C_1$-$C_5$alkyl, and $R_3$ is $CF_3$ or $CF_2H$, which comprises:
aa) reacting 6-nitro-anthranilic acid with a nitrite selected from isoamyl nitrite and tert-butyl nitrite, and with a compound of formula C:

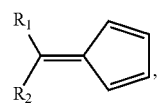

wherein $R_1$ and $R_2$ are as defined for formula I, to form a compound of formula II:

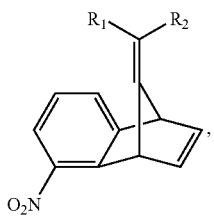
(II)

wherein $R_1$ and $R_2$ are as defined for formula I;
a) reacting the compound of formula II with a reducing agent to form a compound of formula III:

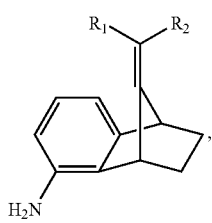
(III)

wherein $R_1$ and $R_2$ are as defined for formula I;
(b) reacting the compound of formula III with at least one reducing agent to form a compound of formula IV:

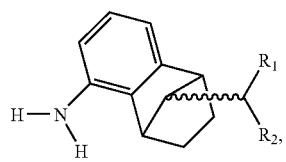
(IV)

wherein $R_1$ and $R_2$ are as defined for formula I; and
(c) converting the compound of formula IV into the compound of formula I by reaction with a compound of formula V:

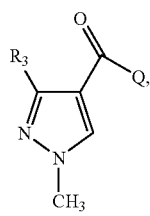
(V)

wherein Q is chlorine, bromine, iodine or hydroxy and $R_3$ is as defined for formula I.

11. A process according to claim 10 for the preparation of a compound of formula I wherein $R_1$ and $R_2$ are methyl and $R_3$ is $CF_2H$, which comprises:
  aa) reacting 6-nitro-anthranilic acid with tert-butyl nitrite and with a compound of formula C wherein $R_1$ and $R_2$ are methyl to form a compound of formula II wherein $R_1$ and $R_2$ are methyl;
  a) reacting the compound of formula II with hydrogen in the presence of a rhodium/carbon catalyst to form a compound of formula III wherein $R_1$ and $R_2$ are methyl;
  (b) reacting the compound of formula III with hydrogen in the presence of a Raney nickel catalyst to form a compound of formula IV wherein $R_1$ and $R_2$ are methyl; and
  (c) converting the compound of formula IV into the compound of formula I by reaction with a compound of formula V wherein Q is hydroxy and $R_3$ is $CF_2H$, in the presence of an activating agent, the reaction being carried out in the presence of a base.

12. A process for the preparation of a compound of formula I:

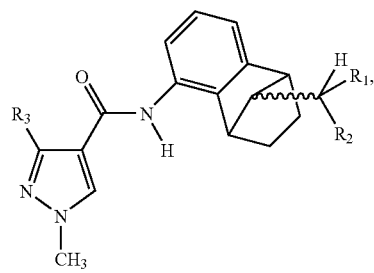
(I)

wherein $R_1$ and $R_2$ are each independently hydrogen or $C_1$-$C_5$alkyl, and $R_3$ is $CF_3$ or $CF_2H$, which comprises:
  a) reacting a compound of formula II:

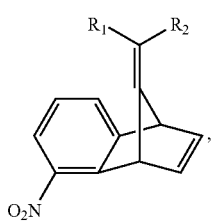
(II)

wherein $R_1$ and $R_2$ are as defined for formula I, with a reducing agent to form a compound of formula III:

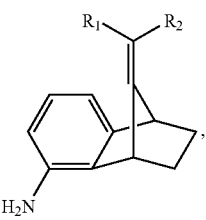
(III)

wherein $R_1$ and $R_2$ are as defined for formula I;
  b) reacting the compound of formula III with at least one reducing agent to form a compound of formula IV:

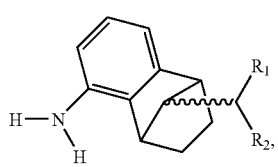
(IV)

wherein $R_1$ and $R_2$ are as defined for formula I;
  d) reacting a compound of formula Va:

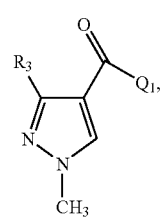
(Va)

wherein $Q_1$ is chlorine, fluorine, bromine, iodine or $C_1$-$C_6$alkoxy and $R_3$ is as defined for formula I, with a compound of formula VII:

 (VII), wherein L is as defined for formula VI, to form a compound of formula VI:

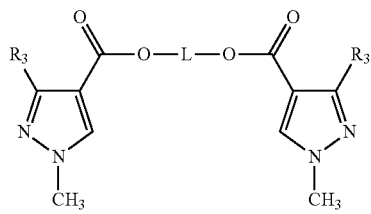 (VI)

wherein L is a $C_1$-$C_6$alkylene chain and $R_3$ is as defined for formula I; and e) converting the compound of formula VI into the compound of formula I by reaction with the compound of formula IV.

13. A process according to claim 1, wherein in said step of reacting the compound of formula III, hydrogen in the presence of a rhodium catalyst is used as the reducing agent.

14. A process according to claim 10, wherein in said step of reacting the compound of formula III, hydrogen in the presence of a rhodium catalyst is used as the reducing agent.

15. A process according to claim 12, wherein in said step of reacting the compound of formula III, hydrogen in the presence of a rhodium catalyst is used as the reducing agent.

\* \* \* \* \*